(12) United States Patent
Parunak et al.

(10) Patent No.: US 7,270,786 B2
(45) Date of Patent: Sep. 18, 2007

(54) METHODS AND SYSTEMS FOR PROCESSING MICROFLUIDIC SAMPLES OF PARTICLE CONTAINING FLUIDS

(75) Inventors: Gene Parunak, Ann Arbor, MI (US); Kalyan Handique, Ann Arbor, MI (US); Betty Wu, Canton, MI (US); Aaron Kehrer, Ann Arbor, MI (US)

(73) Assignee: HandyLab, Inc., Ann Arbor, MI (US)

( * ) Notice: Subject to any disclaimer, the term of this patent is extended or adjusted under 35 U.S.C. 154(b) by 71 days.

(21) Appl. No.: 10/014,520

(22) Filed: Dec. 14, 2001

(65) Prior Publication Data

US 2002/0141903 A1    Oct. 3, 2002

Related U.S. Application Data

(63) Continuation-in-part of application No. 09/953,921, filed on Sep. 18, 2001, now Pat. No. 6,575,188, and a continuation-in-part of application No. 09/819,105, filed on Mar. 28, 2001, now Pat. No. 7,010,391.

(60) Provisional application No. 60/307,638, filed on Jul. 26, 2001.

(51) Int. Cl.
*B32B 5/02* (2006.01)
*B32B 27/04* (2006.01)
*B32B 27/12* (2006.01)
*G01N 21/00* (2006.01)
*G01N 31/00* (2006.01)

(52) U.S. Cl. .............. 422/81; 422/50; 422/55; 422/56; 422/57; 422/58; 422/61; 422/68.1; 422/82; 422/82.05; 422/82.09; 422/100; 422/101; 422/102; 422/103; 422/104; 435/283.1; 435/285.2; 435/287.1; 435/287.3; 435/288.7; 436/43; 436/63; 436/501; 436/86; 436/89; 436/94

(58) Field of Classification Search .............. 422/50, 422/55, 56, 57, 58, 61, 68.1, 81, 82, 82.05, 422/82.09, 100–104; 435/283.1, 285.2, 287.1, 435/287.3, 288.7; 436/501, 43, 63, 86, 89, 436/94
See application file for complete search history.

(56) References Cited

U.S. PATENT DOCUMENTS

| | | | |
|---|---|---|---|
| 1,616,419 A | 2/1927 | Wilson | 137/251.1 |
| 1,773,401 A | 8/1930 | Lovekin | 137/74 |
| 3,528,449 A | 9/1970 | Witte et al. | 137/251.1 |
| 4,139,005 A | 2/1979 | Dickey | 138/74 |
| 4,612,959 A | 9/1986 | Costello | 137/251.1 |

(Continued)

OTHER PUBLICATIONS

Handique and Burns, 2001, "Mathematical Modeling of Drop Mixing in a Slit-Type Microchannel", J. Micromech. Microeng. 11:548-554.
Handique et al., 2001, "On-Chip Thermopneumatic Pressure for Discrete Drop Pumping," Anal. Chem. 73:1831-1838.

(Continued)

*Primary Examiner*—Brian Sines
(74) *Attorney, Agent, or Firm*—Fish & Richardson P.C.

(57) ABSTRACT

The present invention relates to a microfluidic system for processing a cell-containing liquid. The system includes a microfabricated substrate having an enrichment channel to prepare an enriched cell sample from the cell-containing liquid. A flow through member is in liquid communication with the enrichment zone. The flow through member substantially prevents cells of the cell-containing fluid from exiting the enrichment zone while allowing liquid of the cell-containing liquid to exit the enrichment zone. A gas actuator associated with the enrichment zone provides a gas pressure sufficient to move the enriched cell sample from the enrichment zone.

42 Claims, 15 Drawing Sheets

U.S. PATENT DOCUMENTS

| | | | | |
|---|---|---|---|---|
| 4,654,127 | A | 3/1987 | Baker et al. | 204/1 T |
| 4,673,657 | A | 6/1987 | Christian | 436/501 |
| 4,946,562 | A | 8/1990 | Guruswamy | 204/153.1 |
| 4,949,742 | A | 8/1990 | Rando et al. | 137/828 |
| 4,963,498 | A | 10/1990 | Hillman et al. | 436/69 |
| 4,989,626 | A | 2/1991 | Takagi et al. | 137/828 |
| 5,001,417 | A | 3/1991 | Pumphrey et al. | 324/71.5 |
| 5,004,583 | A | 4/1991 | Guruswamy et al. | 422/58 |
| 5,053,199 | A | 10/1991 | Keiser et al. | 422/68.1 |
| 5,061,336 | A | 10/1991 | Soane | 156/245 |
| 5,064,618 | A | 11/1991 | Baker et al. | 422/82.01 |
| 5,071,531 | A | 12/1991 | Soane | 204/182.8 |
| 5,126,002 | A | 6/1992 | Iwata et al. | 156/468 |
| 5,126,022 | A | 6/1992 | Soane et al. | 204/180.1 |
| 5,135,627 | A | 8/1992 | Soane | 204/182.8 |
| 5,135,872 | A | 8/1992 | Pouletty et al. | 436/180 |
| 5,147,606 | A | 9/1992 | Charlton et al. | 422/56 |
| 5,208,163 | A | 5/1993 | Charlton et al. | 436/63 |
| 5,250,263 | A | 10/1993 | Manz | 422/81 |
| 5,282,950 | A | 2/1994 | Dietze et al. | 204/406 |
| 5,296,375 | A | 3/1994 | Kricka et al. | 435/291 |
| 5,304,477 | A | 4/1994 | Nagoh et al. | 435/134 |
| 5,304,487 | A | 4/1994 | Wilding et al. | 435/291 |
| 5,311,896 | A | 5/1994 | Kaartinen et al. | |
| 5,316,727 | A | 5/1994 | Suzuki et al. | 422/68.1 |
| 5,339,486 | A | 8/1994 | Persic, Jr. | 15/244.1 |
| 5,372,946 | A | 12/1994 | Cusak et al. | 436/69 |
| 5,374,395 | A | 12/1994 | Robinson et al. | 422/64 |
| 5,411,708 | A | 5/1995 | Moscetta et al. | 422/81 |
| 5,427,946 | A | 6/1995 | Kricka et al. | 435/291 |
| 5,486,335 | A | 1/1996 | Wilding et al. | 422/55 |
| 5,498,392 | A | 3/1996 | Wilding et al. | 422/68.1 |
| 5,503,803 | A | 4/1996 | Brown | 422/102 |
| 5,519,635 | A | 5/1996 | Miyake et al. | 364/497 |
| 5,559,432 | A | 9/1996 | Logue | 324/207.17 |
| 5,565,171 | A | 10/1996 | Dovichi et al. | 422/68.1 |
| 5,569,364 | A | 10/1996 | Hooper et al. | 204/455 |
| 5,580,523 | A | 12/1996 | Bard | 422/50 |
| 5,585,069 | A | 12/1996 | Zanzucchi et al. | 422/100 |
| 5,585,089 | A | 12/1996 | Queen et al. | 424/133.1 |
| 5,587,128 | A | 12/1996 | Wilding et al. | 422/50 |
| 5,589,136 | A | 12/1996 | Northrup et al. | 422/102 |
| 5,593,838 | A | 1/1997 | Zanzucchi et al. | 435/6 |
| 5,599,432 | A | 2/1997 | Manz et al. | 204/451 |
| 5,599,503 | A | 2/1997 | Manz et al. | 422/82.05 |
| 5,603,351 | A | 2/1997 | Cherukuri et al. | 137/597 |
| 5,605,662 | A | 2/1997 | Heller et al. | 422/68.1 |
| 5,628,890 | A | 5/1997 | Carter et al. | 204/403 |
| 5,631,337 | A | 5/1997 | Sassi et al. | 526/307.2 |
| 5,632,876 | A | 5/1997 | Zanzucchi et al. | 204/600 |
| 5,632,957 | A | 5/1997 | Heller et al. | 422/68.1 |
| 5,635,358 | A | 6/1997 | Wilding et al. | 435/7.2 |
| 5,637,469 | A | 6/1997 | Wilding et al. | 435/7.21 |
| 5,639,423 | A | 6/1997 | Northrup et al. | 122/50 |
| 5,643,738 | A | 7/1997 | Zanzucchi et al. | 435/6 |
| 5,646,039 | A | 7/1997 | Northrup et al. | 435/287.2 |
| 5,652,149 | A | 7/1997 | Mileaf et al. | 436/518 |
| 5,674,742 | A | 10/1997 | Northrup et al. | 435/286.5 |
| 5,681,484 | A | 10/1997 | Zanzucchi et al. | 216/2 |
| 5,681,529 | A | 10/1997 | Taguchi et al. | 422/61 |
| 5,683,657 | A | 11/1997 | Mian | 422/68.1 |
| 5,699,157 | A | 12/1997 | Parce | 356/344 |
| 5,726,026 | A | 3/1998 | Wilding et al. | 435/7.21 |
| 5,726,404 | A * | 3/1998 | Brody | 200/81 R |
| 5,731,212 | A | 3/1998 | Gavin et al. | 436/526 |
| 5,747,666 | A | 5/1998 | Willis | 73/1.02 |
| 5,750,015 | A | 5/1998 | Soane et al. | 204/454 |
| 5,755,942 | A | 5/1998 | Zanzucchi et al. | 204/454 |
| 5,763,262 | A | 6/1998 | Wong et al. | 435/287.2 |
| 5,770,029 | A | 6/1998 | Nelson et al. | 204/604 |
| 5,772,966 | A | 6/1998 | Maracas et al. | 422/100 |
| 5,779,868 | A | 7/1998 | Parce et al. | 204/604 |
| 5,787,032 | A | 7/1998 | Heller et al. | 365/151 |
| 5,788,814 | A | 8/1998 | Sun et al. | 204/297 |
| 5,800,690 | A | 9/1998 | Chow et al. | 204/451 |
| 5,827,481 | A | 10/1998 | Bente et al. | 422/81 |
| 5,842,106 | A | 11/1998 | Thaler et al. | 419/8 |
| 5,842,787 | A | 12/1998 | Kopf-Sill et al. | 366/340 |
| 5,846,396 | A | 12/1998 | Zanzucchi et al. | 204/601 |
| 5,849,486 | A | 12/1998 | Heller et al. | 435/6 |
| 5,849,489 | A | 12/1998 | Heller | 435/6 |
| 5,849,598 | A | 12/1998 | Wilson et al. | 436/180 |
| 5,852,495 | A | 12/1998 | Parce | 356/344 |
| 5,856,174 | A | 1/1999 | Lipshutz et al. | 435/286.5 |
| 5,858,188 | A | 1/1999 | Soane et al. | 204/454 |
| 5,863,502 | A | 1/1999 | Southgate et al. | 422/58 |
| 5,863,708 | A | 1/1999 | Zanzucchi et al. | 430/320 |
| 5,863,801 | A | 1/1999 | Southgate et al. | 436/63 |
| 5,866,345 | A | 2/1999 | Wilding et al. | 435/7.21 |
| 5,869,004 | A | 2/1999 | Parce et al. | 422/100 |
| 5,872,010 | A | 2/1999 | Karger et al. | 436/173 |
| 5,874,046 | A | 2/1999 | Megerle | 422/68.1 |
| 5,876,675 | A | 3/1999 | Kennedy | 422/99 |
| 5,880,071 | A | 3/1999 | Parce et al. | 204/453 |
| 5,882,465 | A | 3/1999 | McReynolds | 156/285 |
| 5,883,211 | A | 3/1999 | Sassi et al. | 526/307.2 |
| 5,885,432 | A | 3/1999 | Hooper et al. | 204/469 |
| 5,885,470 | A | 3/1999 | Parce et al. | 216/33 |
| 5,895,762 | A | 4/1999 | Greenfield et al. | 436/43 |
| 5,900,130 | A | 5/1999 | Benregnu et al. | 204/453 |
| 5,912,124 | A | 6/1999 | Kumar | 435/6 |
| 5,912,134 | A | 6/1999 | Shartle | 435/7.24 |
| 5,916,522 | A | 6/1999 | Boyd et al. | 422/58 |
| 5,916,776 | A | 6/1999 | Kumar | 435/91.1 |
| 5,919,711 | A | 7/1999 | Boyd et al. | 436/178 |
| 5,922,591 | A | 7/1999 | Anderson et al. | 435/287.2 |
| 5,927,547 | A | 7/1999 | Papen et al. | 222/57 |
| 5,928,880 | A | 7/1999 | Wilding et al. | 435/7.21 |
| 5,929,208 | A | 7/1999 | Heller et al. | 530/333 |
| 5,932,799 | A | 8/1999 | Moles | 75/53.01 |
| 5,935,401 | A | 8/1999 | Amigo | 204/454 |
| 5,939,291 | A | 8/1999 | Loewy et al. | 435/91.2 |
| 5,942,443 | A | 8/1999 | Parce et al. | 436/514 |
| 5,948,227 | A | 9/1999 | Dubrow | 204/455 |
| 5,955,028 | A | 9/1999 | Chow | 422/63 |
| 5,955,029 | A | 9/1999 | Wilding et al. | 422/68.1 |
| 5,957,579 | A | 9/1999 | Kopf-Sill et al. | 366/340 |
| 5,958,203 | A | 9/1999 | Parce et al. | 204/451 |
| 5,958,694 | A | 9/1999 | Nikiforov | 435/6 |
| 5,959,291 | A | 9/1999 | Jensen | 250/214 |
| 5,964,995 | A | 10/1999 | Nikiforov et al. | 204/450 |
| 5,964,997 | A | 10/1999 | McBride | 204/451 |
| 5,965,001 | A | 10/1999 | Chow et al. | 204/600 |
| 5,965,410 | A | 10/1999 | Chow et al. | 435/91.2 |
| 5,965,886 | A | 10/1999 | Sauer et al. | 250/332 |
| 5,972,187 | A | 10/1999 | Parce et al. | 204/453 |
| 5,976,336 | A | 11/1999 | Dubrow et al. | 204/453 |
| 5,980,704 | A | 11/1999 | Cherukuri et al. | 204/269 |
| 5,980,719 | A | 11/1999 | Cherukuri et al. | 204/600 |
| 5,989,402 | A | 11/1999 | Chow et al. | 204/601 |
| 5,992,820 | A | 11/1999 | Fare et al. | 251/129.01 |
| 5,993,611 | A | 11/1999 | Moroney, III et al. | 204/157.6 |
| 5,993,750 | A | 11/1999 | Ghosh et al. | 422/191 |
| 5,997,708 | A | 12/1999 | Craig | 204/601 |
| 6,001,231 | A | 12/1999 | Kopf-Sill | 204/454 |
| 6,001,307 | A | 12/1999 | Naka et al. | 422/81 |
| 6,004,515 | A | 12/1999 | Parce et al. | 422/100 |
| 6,007,690 | A * | 12/1999 | Nelson et al. | 204/601 |
| 6,012,902 | A | 1/2000 | Parce | 417/48 |
| 6,043,080 | A | 3/2000 | Lipshutz et al. | 435/287.2 |
| 6,046,056 | A | 4/2000 | Parce et al. | 436/514 |
| 6,048,734 | A | 4/2000 | Burns et al. | 436/180 |
| 6,054,034 | A | 4/2000 | Soane et al. | 204/601 |
| 6,056,860 | A | 5/2000 | Amigo et al. | 204/454 |

| | | | |
|---|---|---|---|
| 6,057,149 A | 5/2000 | Burns et al. | 435/287.2 |
| 6,102,897 A | 8/2000 | Lang et al. | |
| 6,130,098 A | 10/2000 | Handique et al. | 436/180 |
| 6,168,948 B1 | 1/2001 | Anderson et al. | 435/287.2 |
| 6,197,595 B1 * | 3/2001 | Anderson et al. | 436/180 |
| 6,287,254 B1 | 9/2001 | Dodds | 600/300 |
| 6,306,273 B1 | 10/2001 | Wainright et al. | 204/454 |
| 6,326,211 B1 | 12/2001 | Anderson et al. | |
| 6,534,295 B2 * | 3/2003 | Tai et al. | 435/173.7 |
| 6,544,734 B1 * | 4/2003 | Briscoe et al. | 435/6 |
| 6,572,830 B1 | 6/2003 | Burdon et al. | |
| 2002/0054835 A1 | 5/2002 | Robotti et al. | |
| 2002/0055167 A1 * | 5/2002 | Pourahmadi et al. | 435/287.2 |

OTHER PUBLICATIONS

Handique et al., 2000, "Nanoliter Liquid Metering in Microchannels Using Hydrophobic Patterns," Anal. Chem. 72:4100-4109.

Burns et al., 1998, "An Integrated Nanoliter DNA Analysis Device," Science 282:484-487.

B. Scott Broyles et al., "Sample Filtration, Concentration, and Separation Integrated on Microfluidic Devices", *Anal. Chem.*, vol. 75:11, pp. 2761-2767 (2003).

Supplementary European Search Report dated Jun. 3, 2005.

Jörg P. Kutter et al., Solid Phase Extraction on Microfluidic Devices, *J. Microcolumn Separations*, 2000 12(2), pp. 93-97.

Richard D. Oleschuk et al., Trapping of Bead-Based Reagents within Microfluidic Systems: On-Chip Solid-Phase Extraction and Electrochromatography, Anal. Chem. 2000, 72, pp. 585-590.

M. Sofi Ibrahim et al., Real-Time Microchip PCR for Detecting Single-Base Differences in Viral and Human DNA, Anal. Chem. 1998, 70, pp. 2013-2017.

Martin U. Kopp et al., Chemical Amplification: Continuous-Flow PCR on a Chip, SCIENCE, www.sciencemag.org., vol. 280, May 15, 1998, pp. 1046-1048.

M. Allen Northrup et al., A Miniature Analytical Instrument for Nucleic Acids Based on Micromachined Silicon Reaction Chambers, Analytical Chemistry, vol. 70, No. 5, Mar. 1, 1998, pp. 918-922.

Philip L. Ross et al., Analysis of DNA Fragments from Conventional and Microfabricated PCR Devices Using Delayed Extraction MALDI-TOF Mass Spectrometry, Anal. Chem. 1998, 70, pp. 2067-2073.

Larry C. Waters et al., Microchip Device for Cell Lysis, Multiplex PCR Amplification, and Electrophoretic Sizing, Anal. Chem. 1998, 70, pp. 158-162.

E.T. Lagally et al., Single-Molecule DNA Amplification and Analysis in an Integrated Microfluidic Device, Anal. Chem. 2001, 73, pp. 565-570.

Julia Khandurina et al., Microfabricated Porous Membrane Structure for Sample Concentration and Electrophoretic Analysis, Anal. Chem. 1999, 71, pp. 1815-1819.

Bing He et al., Microfabricated Filters for Microfluidic Analytical Systems, Anal. Chem. 1999, 71, pp. 1464-1468.

James P. Brody et al., Diffusion-based extraction in a microfabricated device, Sensors and Actuators, vol. A58, No. 1, Jan. 1997, pp. 13-18.

Bernhard H. Weigl et al., Microfluidic Diffusion-Based Separation and Detection, SCIENCE, www.sciencemag.org, Jan. 15, 1999, vol. 283, pp. 346-347.

* cited by examiner

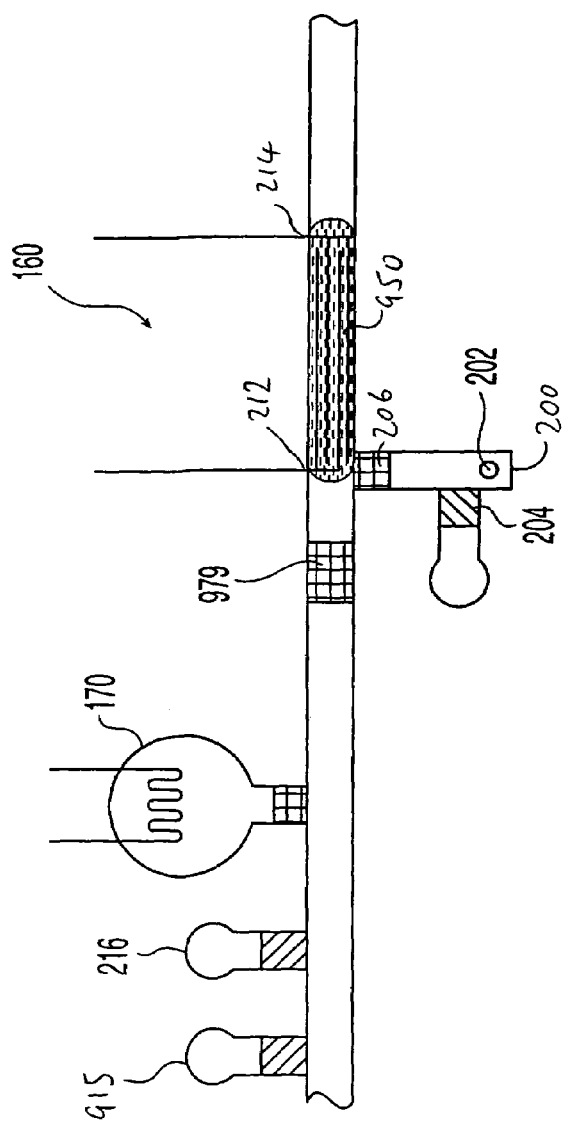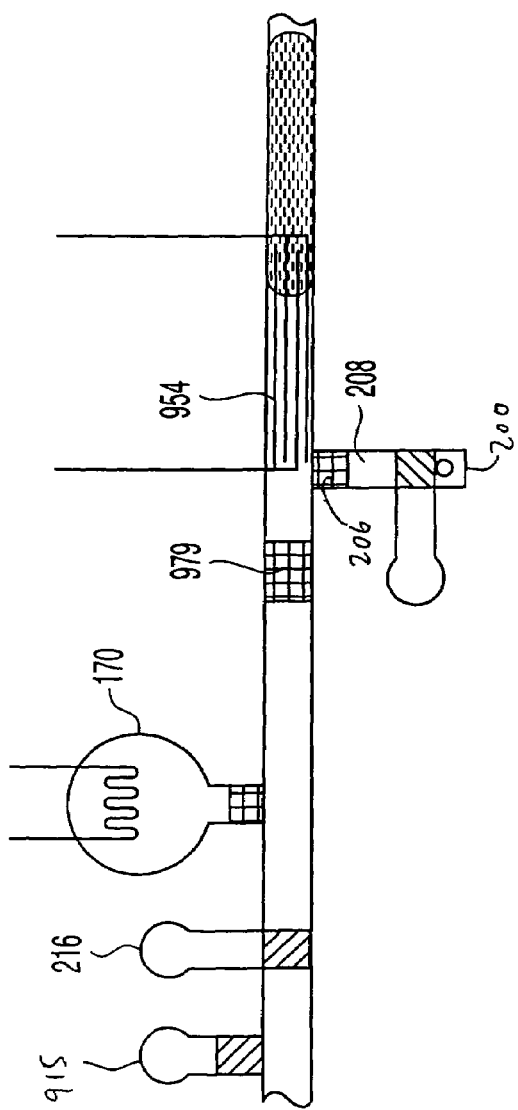

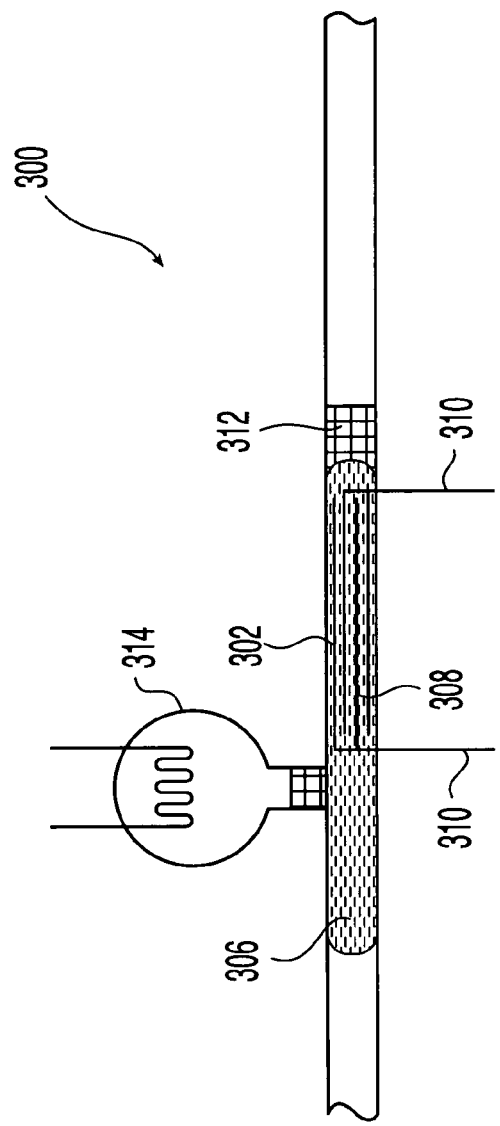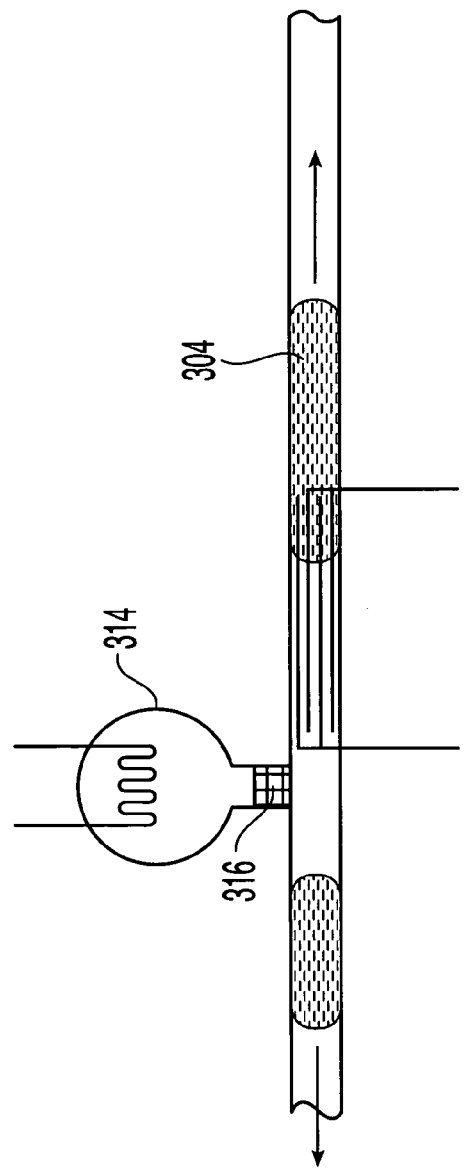

METHODS AND SYSTEMS FOR PROCESSING MICROFLUIDIC SAMPLES OF PARTICLE CONTAINING FLUIDS

RELATED APPLICATIONS

This application is a continuation-in-part of application Ser. No. 09/953,921, filed Sep. 18, 2001 now U.S. Pat. No. 6,575,188, and claims priority of provisional application No. 60/307,638 filed Jul. 26, 2001. This application is also a continuation-in-part of application Ser. No. 09/819,105, filed Mar. 28, 2001 now U.S. Pat. No. 7,010,391. Each of the above-mentioned applications are incorporated herein by reference.

FIELD OF THE INVENTION

The present invention relates to methods and systems for processing samples using microfluidic systems. More particularly, the invention relates to microfluidic systems for processing fluid samples containing particles, such as cells.

BACKGROUND

Microfluidic devices are typically formed of substrates (made of silicon, glass, ceramic, plastic and/or quartz) which include a network of micro-channels through which fluid flows under the control of a propulsion mechanism. The micro channels typically have at least one dimension which is on the order of nanometers to hundreds of microns.

Microfluidic devices process minute amounts of fluid sample to determine the physical and chemical properties of the sample. Microfluidic devices offer several advantages over a traditional macro-scale instrumentation. For example, in general, they require substantial smaller fluid samples, use far less reagent, and process these fluids at substantially greater speeds than macro-scale equipment.

In many cases, the accuracy of such fluid processing depends upon the relative amounts of sample and reagent used. For example, when a sample is analyzed for a DNA "fingerprint," the results may depend upon the concentration of reagents used to amplify DNA present in the sample. Thus, if an improper ratio of sample to reagent is used, the result may be inaccurate. Because microfluidic devices process samples and reagents in minute amounts, even a small absolute uncertainty in the amount of reagent or sample used can introduce uncertainty to the results of a microfluidic analysis.

Variances in the amount of samples and reagents processed by a microfluidic device may originate from several sources. For example, some microfluidic devices manipulate continuous, flowing streams of liquid. Changes in the viscosity of the liquid can alter the flow rate of the streams and, correspondingly, the time required to introduce a predetermined amount of material to a given location of the microfluidic device. Sample dilution may occur where a liquid flow stream is used to move sample components from one location to another within a microfluidic device.

Microfluidic analysis of particles suspended in a fluid (such as cells within body fluids) is especially challenging due to the relatively small number of particles available for analysis and the inherent difficulty in manipulating such fluids.

SUMMARY OF THE INVENTION

In general, the present invention relates to a microfluidic system and method for processing a particle-containing fluid, such as, for example, a liquid containing bacterial cells or human cells.

In one aspect, the invention relates to preparing an enriched particle sample from the particle-containing fluid. For example, a microfluidic system for preparing an enriched sample includes an enrichment zone and a flow through member disposed in fluid communication with the enrichment zone. The flow through member allows fluid of the particle containing fluid to pass through and exit the enrichment zone, while causing particles of the particle-containing fluid to accumulate within the zone, thereby preparing an enriched particle sample in the enrichment zone. The flow through member may include a plurality of pathways, such as pores, having a sufficient size to allow passage of the fluid therethrough but of a size too small to allow passage of the particles therethrough. Suitable flow through members are composed of, for example, filter elements, such as filter paper, porous glasses, and porous gels.

The microfluidic system may include an actuator that moves the enriched particle sample from the enrichment zone with essentially no dilution of the enriched particle sample. In one embodiment, the actuator is a gas actuator that moves the sample by increasing a gas pressure associated with an upstream portion of the enrichment zone relative to a gas pressure associated with the downstream channel. For example, the gas actuator may include a source of heat in thermal contact with a volume of gas. Expansion of the gas upon actuating the heat source creates a gas pressure sufficient to move the enriched particle sample from the enrichment zone to another location within the microfluidic system, such as a location containing modules for further fluid processing.

In another aspect, the invention relates to a microfluidic system and method for processing an enriched particle sample which includes cells entrained in a liquid. For example, the system includes a lysing zone to receive the enriched cell-containing sample and a positioning element to position the enriched cell-containing sample in a lysing position in the vicinity of a lysing mechanism. The lysing mechanism releases intracellular material, such as DNA or RNA, from the cells. In one embodiment, the lysing mechanism includes electrodes for generating an electric field sufficient to release intracellular contents from the cells. Alternatively, the lysing mechanism may lyse the cells using chemical, heat and/or ultrasonic techniques or any combination of these techniques.

In one embodiment, the lysing zone releases intracellular contents from cells of the cell-containing fluid and then prepares from this fluid a microdroplet which contains intracellular contents released from the cells. The microdroplet is preferably prepared from only a portion of the cell-containing fluid. For example, a preferred microdroplet includes less than about 90 percent of the cell-containing fluid. In another embodiment, the lysing zone receives a microdroplet of cell-containing fluid and releases the intracellular contents of the cells within the droplet.

In another aspect, the invention relates to a microfluidic substrate for processing the intracellular contents of cells suspended in fluids. The substrate includes an enrichment zone, a lysing module, a microdroplet formation module, mixing module and an amplificaition module. The enrichment zone preparing an enriched particle sample from the cell-containing fluid. The lysing module, which is coupled to the enrichment zone for receiving the enriched particle sample, releases intracellular material from cells within the sample to thereby forming a lyced sample. The microdroplet formation module then forms a first microdroplet of fluid from the lysed sample and forwards it to a mixing module for mixing with a microdroplet of reagent. The amplification module amplifies intercellular material within the microdroplet formed from the mixture.

BRIEF DESCRIPTION OF THE DRAWINGS

The present invention is described below in reference to the following drawings, in which:

FIG. 8b shows cross sectional view of the microdroplet preparation zone of FIG. 8a;

FIG. 9b shows a cross sectional side view of the microdroplet preparation zone of FIG. 9a;

FIGS. 12a and 12b show top views of the lysing module of the microfluidic device of FIG. 4, before and after preparation of a lysed sample;

FIGS. 13a and 13b show a second embodiment of a lysing module of the invention;

DETAILED DESCRIPTION OF A PREFERRED EMBODIMENT

The present invention relates to microfluidic systems and methods for processing materials, such as samples and reagents. More specifically, the invention relates to microfluidic systems and methods for processing particle containing fluids. The fluid component of the particle-containing fluid is a gas or, preferably, a liquid. In either case, the fluid entrains particles, which tend to move with the fluid. The particles of the particle-containing fluid are preferably whole cells, such as bacterial cells or cells of an animal, such as a human. However, they may include intracellular material from such cells. For example, a system of the invention may be used to process a sample of bacterial cells to determine whether the bacteria are pathogenic.

A. System Overview

Figure 1:
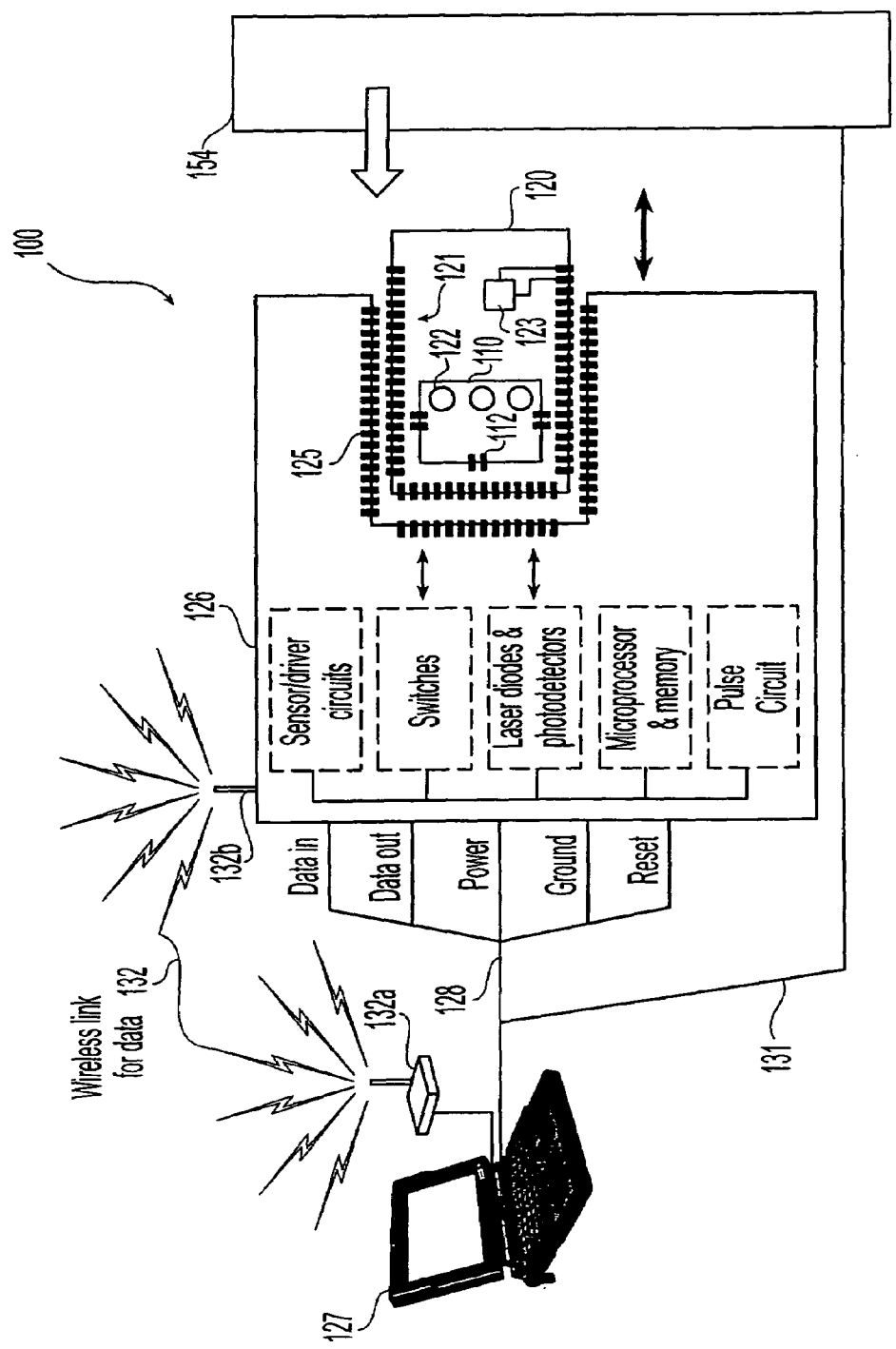
FIG. 1 shows a microfluidic system according to the invention.

FIG. 1 depicts a microfluidic system 100 that includes a microfluidic device 110 and corresponding cartridge 120, which receive one or more fluid samples and process the samples under the control of computer 127 and data acquisition and control board (DAQ) 126.

Computer 127 preferably performs high level functions, such as supplying a user interface that allows a user to select desired operations, notifying the DAQ 126 as to the selected operations, and displaying for the user the results of such operations. These operations include, for example, subjecting a sample to process steps within the various process zones of the microfluidic device. The computer 127 may be a portable computer to facilitate transport of the microfluidic system.

Computer 127 is connected to DAQ 126 via connection 128, which provides data I/O, power, ground, reset, and other functional connectivity. Alternatively, a wireless link 132 between the computer 127 and the DAQ 126 may be provided for data and control signal exchange via wireless elements 132(a) and 132(b). Where the data link is a wireless link, for example, the DAQ 126 may have separate power source, such as a battery.

In general, DAQ 126 controls the operation of microfluidic device 110 in accordance with the high level instructions received from computer 127. More specifically, to implement a desired operation requested by computer 127, DAQ 126 supplies the appropriate electrical control signals to cartridge 120 via contacts 125.

Cartridge 120 provides electrical and optical connections 121 for electrical and optical signals between the DAQ 126 and the microfluidic substrate 110, thereby allowing DAQ 126 to control the operation of the substrate.

The chip carrier cartridge 120 is shown being inserted into (or removed from) an interface hardware receptacle of the DAQ 126 having electrical and optical contacts 125 standardized to mate with corresponding contacts 121 of the chip carrier cartridge 120. Most contacts are for electrical signals, while certain ones are for optical signals (IR, visible, UV, etc.) in the case of optically monitored or optically excited microfluidic processors. Alternatively (not shown), the entire DAQ 126 may be a single ASIC chip that is incorporated into the Chip Carrier Cartridge 120, wherein contacts 121,125 would become conductive pathways on a printed circuit board.

B. Microfluidic Device

Figure 2:
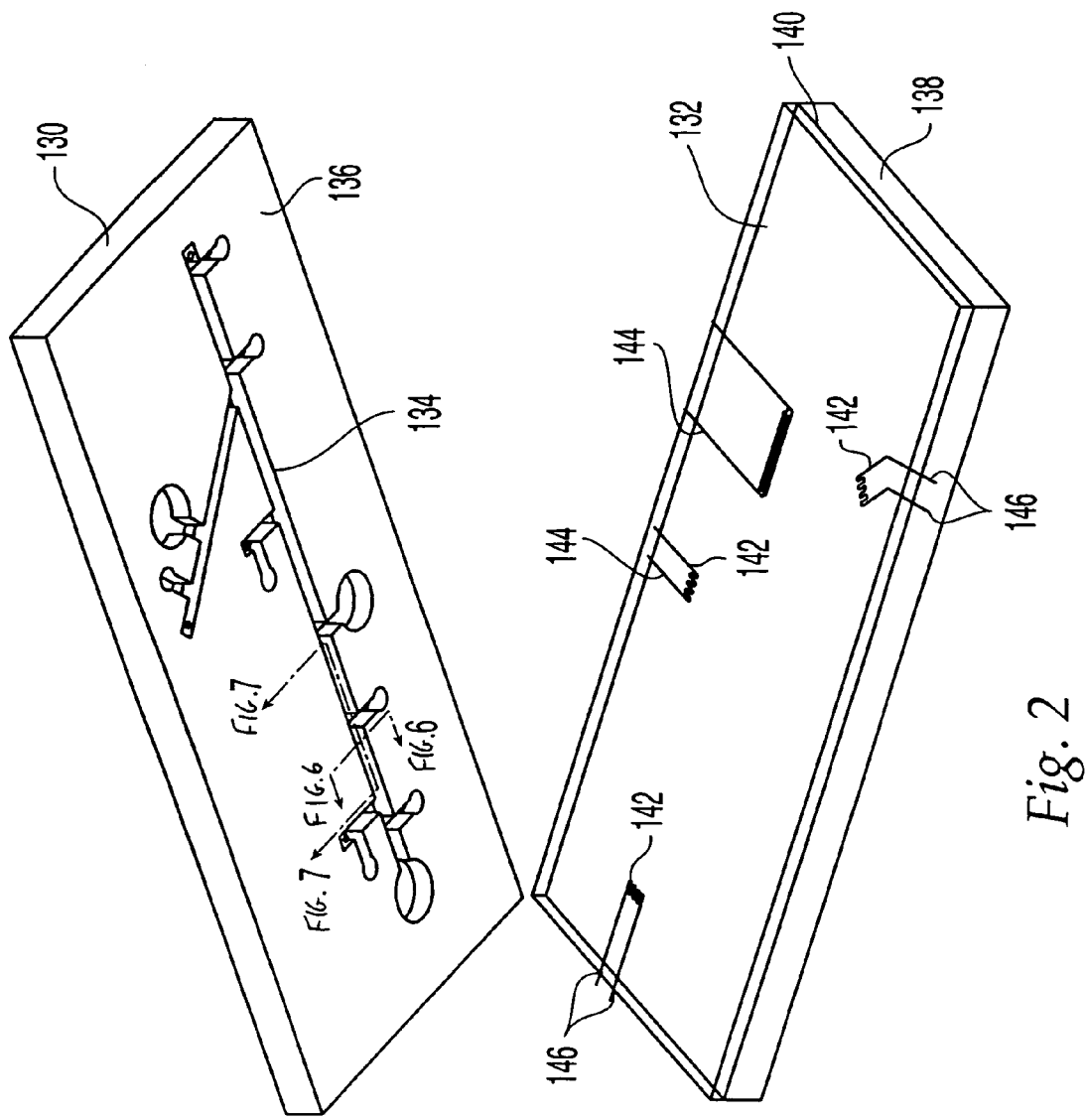
FIG. 2 shows an expanded view of a microfluidic device.

FIG. 2 illustrates the general structure of a preferred type of microfluidic device. The device includes an upper substrate 130, which is bonded to a lower substrate 132 to form a fluid network.

The upper substrate 130 depicted in FIG. 2 is preferably formed of glass and has a microfluidic network 134 in its bottom surface 136. Those skilled in the art will recognize that substrates composed of silicon, glass, ceramic, plastic, and/or quartz are all acceptable in the context of the present invention.

The microfluidic network includes a plurality of zones. The number of zones, as well as the overall topology of the microfluidic network, will depend upon the particular application which the microfluidic device is designed to perform. The zones of the microfluidic device may have any cross-sectional shape, such as generally arcuate or generally polygonal. For example, a zone may include channels, chambers or other substantially enclosed spaces. By "substantially enclosed" it is meant that materials enter or exit the zones only through predetermined pathways. Examples of such pathways include channels, microchannels and the like, which interconnect the various zones. The zones preferably have at least one micro-scale dimension, such as less than about 250 µm or, more preferably, less than about 75 µm.

The channels and chambers of the microfluidic network are etched in the bottom surface 136 of the upper substrate 130 using known photolithographic techniques. More specifically, transparent templates or masks containing opaque designs are used to photo-define objects on the surface of the substrate. The patterns on the templates are generated with computer-aided-design programs and can delineate structures with line-widths of less than one micron. Once a template is generated, it can be used almost indefinitely to produce identical replicate structures. Consequently, even extremely complex microfluidic networks can be reproduced in mass quantities and at low incremental unit cost. Alternatively, if a plastic material is used, the upper substrate may be formed using injection molding techniques, wherein the micro-channels are formed during the molding process.

The lower substrate 132 may include a glass base 138 and an oxide layer 140. Within oxide layer 140, resistive heaters 142 and electric leads 144 are formed using photo-lithographic techniques. The leads 144 connect to terminals 146 which are exposed at the edge of the substrate to permit electrical connection to cartridge 120, thereby permitting DAQ 126 to control the heaters. More specifically, to activate a heater 142, DAQ 126 applies a voltage across a pair of terminals 146 (via cartridge 120) to supply current through leads 146 and heater 142, thereby heating the resistive heater element 142.

Metal heater elements 142 are positioned so that, when the upper and lower substrates are bonded together, the heaters reside directly beneath certain regions of the fluid network of the upper substrate so as to be able to heat the contents of these regions. The silicon oxide layer 140 prevents the heating elements 142 from directly contacting with material in the microfluidic network.

The oxide layer 140, heating elements 142, and resistive leads 144 are fabricated using well-known photolithographic techniques, such as those used to etch the microfluidic network.

Figure 3:
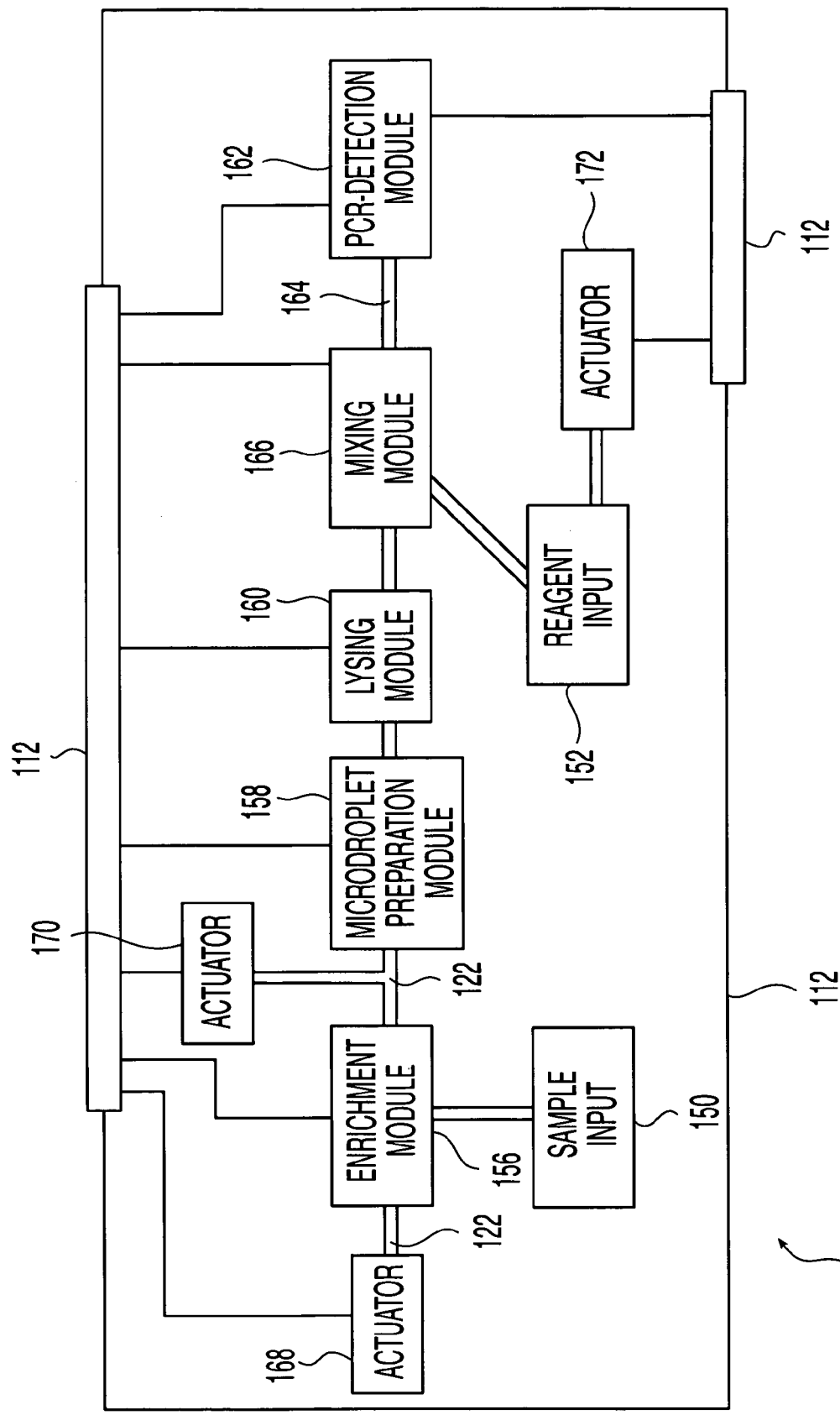
FIG. 3 shows a schematic of a microfluidic device of the microfluidic system of FIG. 1.

FIG. 3 illustrates a top-down view of microfluidic device 110. As shown, the substrate has a sample input module 150 and reagent input module 152 to allow sample and reagent materials, respectively, to be input to device 110. Preferably, input modules 150, 152 are disposed to allow automatic material input using a computer controlled laboratory robot 154.

The substrate also includes process modules 156, 158, 160, 166 and 162 for processing the sample and reagent materials. Within these process modules, a sample may be subjected to various physical and chemical process steps. For example, enrichment module 156 prepares a fluid sample having a relatively high concentration of cell particles, lysing module 160 releases intracellular material from the cell particles, and mixing module 166 mixes the resultant sample with certain reagents. As another example, an amplification process module 162 may be used to amplify and detect minute quantities of DNA within a sample.

Various modules of microfluidic device 110 are connected, such as by channels 164, to allow materials to be moved from one location to another within the device 110. Actuators 168, 170, 172 associated with the microfluidic device provide a motive force, such as a gas pressure, to move the sample and reagent material along the channels and zones. For example, a first actuator 168 moves material downstream from process module 156 to process module 158. Upon completion of processing within process module 158, a second actuator 170 moves material downstream to mixing process module 160. Subsequently, actuator 170 or an additional actuator moves the material to mixing module 166, where the material mixes with a reagent moved by actuator 172. Finally, actuator 172, or another actuator, moves the mixed material to module 162.

Because each actuator is preferably responsible for moving materials within only a subset of the modules of device 110, sample materials can be controlled more precisely than if a single actuator were responsible for moving material throughout the entire device. The various functional elements, of microfluidic device 110, including the actuators, are preferably under computer control to allow automatic sample processing and analysis. Actuators 168, 170. 172 are connected to contacts 112.

1. Enrichment Module a. Structure of Enrichment Module.

Figure 4:
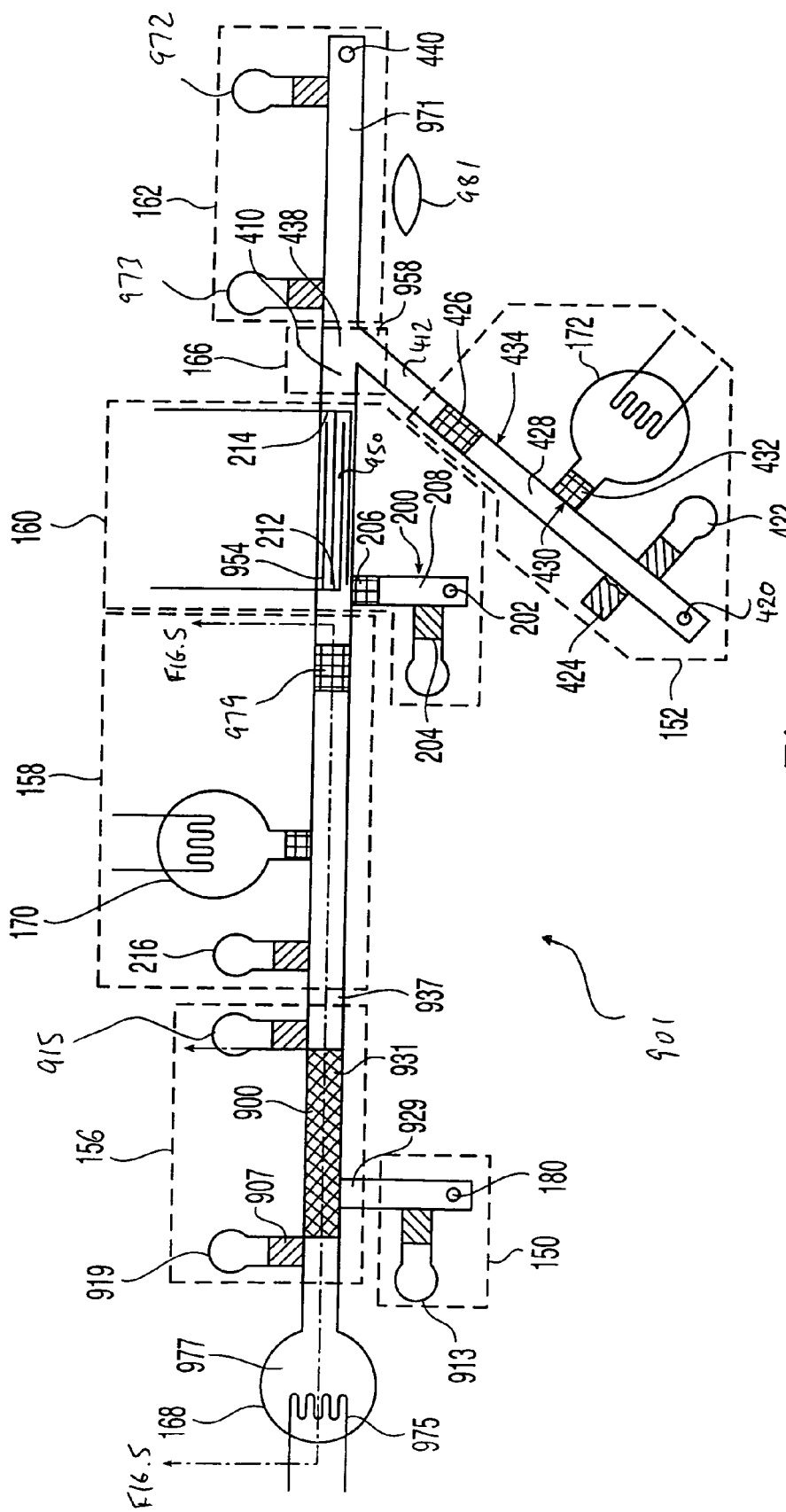
FIG. 4, shows a top view of the microfluidic device of FIG. 3.
Figure 5:
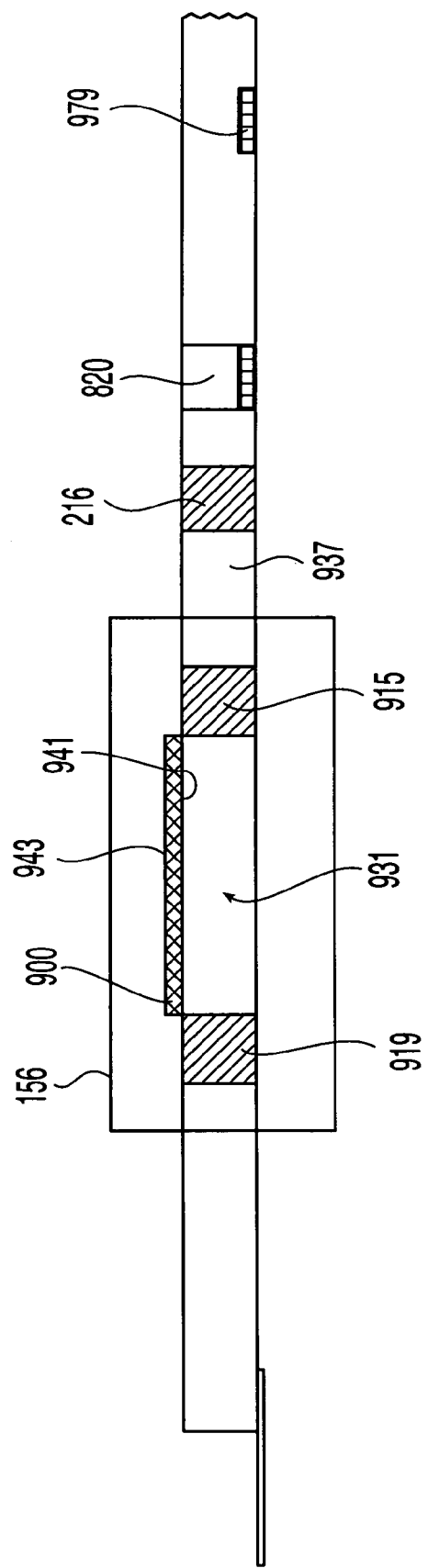
FIG. 5 shows a partial cross-sectional view of the microfluidic device of FIG. 4.

Referring to FIGS. 4 and 5, a microfluidic device 901 includes an enrichment module 156 for concentrating samples received therein. These samples include particle-containing fluids, such as bacterial cell-containing fluids. In general, enrichment module 156 receives a flow of particle-containing fluid from an input port 180 of input module 150, and allows the fluid to pass through the zone while accumulating particles within the zone. Thus, as more fluid flows through the zone, the particle concentration increases within the module. The resultant concentrated fluid sample is referred to herein as an enriched particle sample.

The enrichment module includes an enrichment chamber 931 (FIG. 5), a flow through member 900, valves 915, 919, and sample introduction channel 929. Valve 919 is connected between the flow through member 900 and actuator 168 as shown, and valve 915 is connected between the flow through member and a down stream channel 937 which leads to process module 158. These valves may be of any type suitable for use in a microfluidic device, such as thermally actuated valves, as discussed in co-pending application Ser. No. 09/953,921, filed Sep. 18, 2001. The valves may be reversible between the open and closed states to allow reuse of enrichment module 931.

The flow through member is also connected to the sample input module 150 via the sample introduction channel 929 to allow fluid to flow into the enrichment zone. Valve 913 is connected to this sample introduction channel to control the in-flow and out-flow of fluid from the input port.

FIG. 5 is a cross-sectional view of the enrichment zone which shows the flow through member in greater detail. As shown, flow through member 900 has first and second surfaces 941, 943. First surface 941 is preferably adjacent enrichment chamber 931. Second surface 943 is preferably spaced apart from the enrichment chamber 931 by flow through member 900. Flow through member 900 is preferably formed of a material having pathways smaller than the diameter of the particles to be enriched, such as pores of less than about 2 microns in diameter, for example, about 0.45 microns. Suitable materials for constructing flow through member 900 include, for example, filter media such as paper or textiles, polymers having a network of pathways, and glassy materials, such as glass frits.

Figure 6:
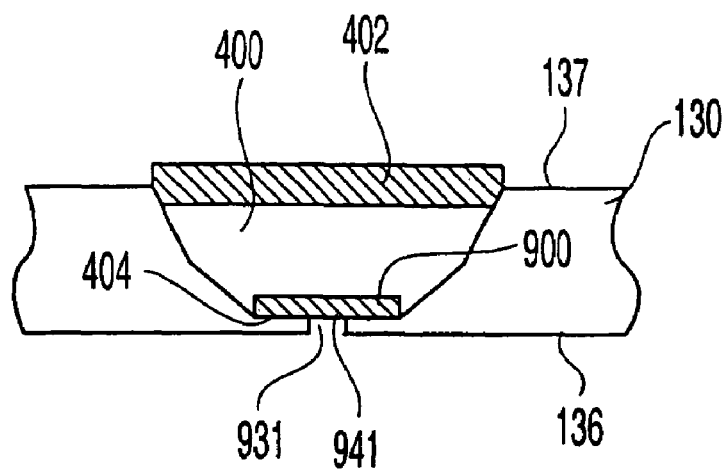
FIG. 6 shows a partial cross-sectional view of an upper substrate from the microfluidic device of FIG. 2.
Figure 7:
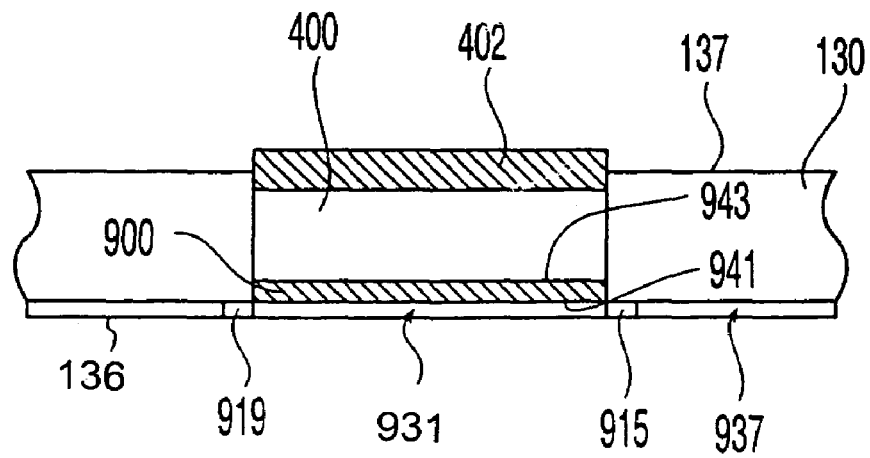
FIG. 7 shows a second partial cross-sectional view of an upper substrate from the microfluidic device of FIG. 2.

FIGS. 6 and 7 depict cross sectional views of upper substrate 130 that illustrate an enrichment zone 931. As shown, fluid exits enrichment zone 931 through surface 941, passes through member 900 and enters a space 400. Space 400 may include an absorbent material 402 to absorb the exiting fluid. Thus, space 400 preferably provides a substantially self-contained region in which fluid exiting the enrichment zone can collect without contacting exterior portions of the microfluidic system 100.

Space 400 is formed during the fabrication of upper substrate 130. As discussed above, microfluidic features, such as zones and channels, are fabricated at surface 136 of substrate 130. Space 400, however, is fabricated at a surface 137, which is preferably disposed on the other side of substrate 130, opposite surface 136. Thus, even when surface 136 is mated with lower substrate 132, fluid can exit enrichment zone 931 via flow through member 900.

Flow through member 900 and absorbent material 402 do not require adhesives or other fasteners for positioning within substrate 130. Rather flow through member 900 and absorbent material 402 may be formed of a shape and size that substantially corresponds to space 400. Friction then holds flow through member 900 and absorbent material 402 in place once they are positioned in space 400. Any residual gap at locations 404 between flow through member 900 and substrate 130 should be small enough to prevent particles from exiting enrichment zone 931 through the gap 404. Naturally, adhesive or other fastening means may be used to secure flow through member 900 or absorbent material 402.

In an alternative embodiment, a flow through member is formed integrally with a substrate by using microfabrication techniques, such as chemical etching, that introduce pores or other pathways into the substrate. The pores provide fluid passage between enrichment zone 931 and an outer portion of the substrate.

b. Operation of Enrichment Module

To enrich a sample, the device 901 operates as follows. Referring to FIG. 4, valves 915, 919 are initially closed, and valve 913 is open. A particle-containing fluid is introduced into input port 180. Since valve 913 is open, it allows the sample to pass along channel 929 into enrichment zone 931. Alternatively, enrichment zone 931 can be configured to receive samples directly, such as by injection. Since valves 915 and 919 are closed, fluid is substantially prevented from escaping into actuator 977 and downstream channel 937.

Thus, flow through member 900 provides the only path for fluid to exit the enrichment channel. Fluid passes through surface 941 and exits enrichment zone 931 via second surface 943, while particles accumulate within the zone. Enrichment zone 931 can therefore receive a volume of fluid that is larger than the volume of the enrichment chamber 931. Thus, as fluid flows through the chamber, the concentration of particles within the chamber increases relative to the concentration in the particle-containing fluid supplied at the sample input. Where the particles are cells, the concentration or number of cells in zone 931 preferably becomes great enough to perform a polymerase chain reaction (PCR) analysis of polynucleotides released from the cells in a downstream processing module.

Enrichment zone 931 thus prepares an enriched particle sample from particles of particle-containing fluids received therein. The enriched particle sample has a substantially higher ratio of particles per volume of fluid (PPVF) than the corresponding ratio of the particle-containing fluid received by the enrichment zone. The PPVF of the enriched particle sample is preferably at least about 25 times, preferably about 250 times, more preferably about 1,000 times greater than the PPVF of the particle-containing fluid.

After a sufficient volume of particle containing fluid has been received by enrichment zone 931, valve 913 is closed thereby blocking further flow of fluid into the enrichment zone, and preventing material in zone 931 from returning to the sample introduction port 180. Valves 915, 919 are then opened, preferably upon actuating heat sources associated therewith. When opened, valve 919 allows actuator 168 to push enriched sample, and valve 915 allows the enriched sample to move downstream.

Actuator 168 provides a motive force that moves the enriched particle sample from enrichment zone 931. Actuator 168 is preferably a gas actuator, which provides a gas pressure upon actuation of a heat source 975, which is in thermal communication with a volume of gas 977. Actuation of heat source 975 raises the temperature and, therefore the pressure, of gas 977. The flow through member and the fluid therein substantially prevents gas from escaping the enrichment zone. Thus, the resulting gas pressure moves the enriched particle sample downstream from the enrichment zone 931.

The gas actuator may include elements to facilitate alternative pressure generation techniques such as chemical pressure generation. In another embodiment, the actuator may decrease a volume of gas associated with an upstream portion of the enrichment zone to thereby create a pressure differential across the sample that moves the sample from the enrichment zone. An example of such an element is a mechanical actuator, such as a plunger or diagram.

Rather than generating a positive pressure upstream from the enrichment zone, the gas actuator may decrease a pressure downstream from the zone relative to a pressure upstream. For example, the gas actuator may include a cooling element in thermal contact with a volume of gas associated with a downstream portion of the zone. Contraction of the gas upon actuating the cooling element creates a gas pressure difference between the upstream and downstream portions of the enrichment zone to move the enriched particle sample from the enrichment zone. Alternatively, a mechanical actuator may be used increase a volume of gas associated with a downstream portion of the enrichment zone to thereby decrease the pressure of the gas and move the enriched particle sample from the enrichment zone.

The enriched particle sample is preferably moved downstream with essentially no dilution thereof, i.e., the concentration of the enriched particles is not substantially decreased upon movement from the enrichment zone 931. Thus, removal of particles from the enrichment channel of the present invention does not require diluting or otherwise contacting the particles with a fluid different from the fluid of the particle-containing fluid introduced to the enrichment channel. In contrast, in systems that concentrate substances by surface adsorption, removal of the adsorbed substances requires an elution fluid, which contacts and thereby dilutes the substances.

Upon removal from the enrichment zone of the present invention, the enriched particle sample is preferably received by downstream channel 937. Downstream channel 937 leads to other processing modules, which perform further processing of the enriched particle sample. In the embodiment of FIG. 3, the enriched particle sample is received by a microdroplet preparation module 158, which prepares a microdroplet sample comprising a portion of the enriched particle sample.

2. Microdroplet Preparation Module a. Characteristics Of A Microdroplet

A microdroplet 802 is a discrete sample having a predetermined volume between, for example, about 1.0 picoliter and about 0.5 microliters. Thus, microdroplets prepared by microdroplet preparation module provide a known amount of sample for further processing. The volume of the microdroplet prepared by the microdroplet preparation module is preferably essentially independent of the viscosity, electrical conductivity, and osmotic strength of the fluid of the microdroplet.

Microdroplet 802 is preferably defined by upstream and downstream boundaries each formed by a respective gas liquid interface 804, 806. The liquid of the interface is formed by a surface of a liquid forming the microdroplet. The gas of the interface is present in the microfluidic channels of microfluidic device 901.

b. Structure and Operation of the Microdroplet Preparation Module

Referring to FIGS. 8a-8b and 9a-9b, microdroplet preparation module 158 prepares a microdroplet 802 from a microfluidic sample received therein. This module includes a microdroplet preparation zone 800, a positioning element 979, a gas actuator 170, and a valve 216 which cooperate to prepare microdroplet 800 from microfluidic samples received from the enrichment zone.

As explained above, actuator 168 of the enrichment zone pushes the enriched sample into the microdroplet preparation zone 800. The enriched sample moves until reaching positioning element 979. In general, a positioning element inhibits the downstream progress of a microfluidic sample to thereby position the sample at a desired location. However, as explained more fully below, the positioning element does not permanently inhibit progress of the sample. Rather, it allows the microfluidic sample to continue downstream at a predetermined later time.

The leading edge of microfluidic sample 808 that reaches positioning element 979 is positioned downstream from an opening 820 of gas actuator 170. Accordingly, a first portion 821 of microfluidic sample 808 is disposed upstream from opening 820 and a second portion 822 of microfluidic sample 808 is disposed downstream from opening 820.

Figure 8A:
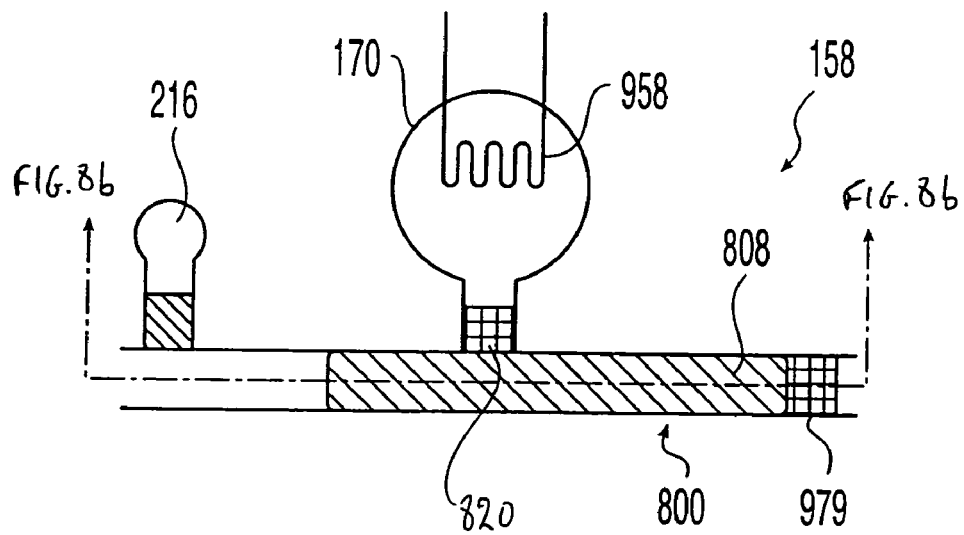
FIG. 8a shows a top view of a microdroplet preparation zone of the microfluidic device of FIG. 4 before preparation of a microdroplet.
Figure 8B:
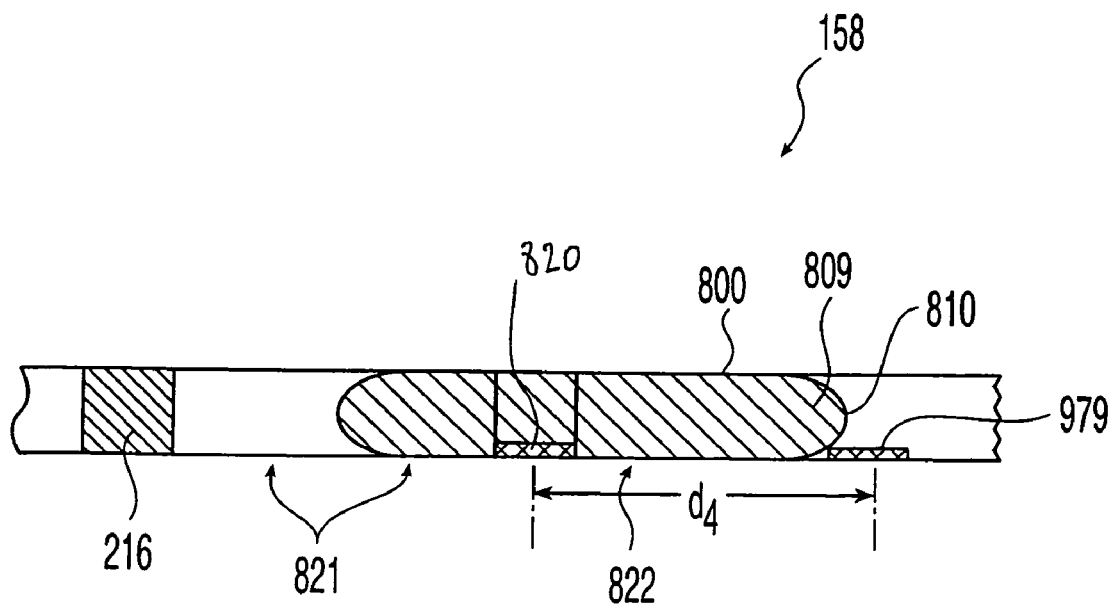
Figure 9A:
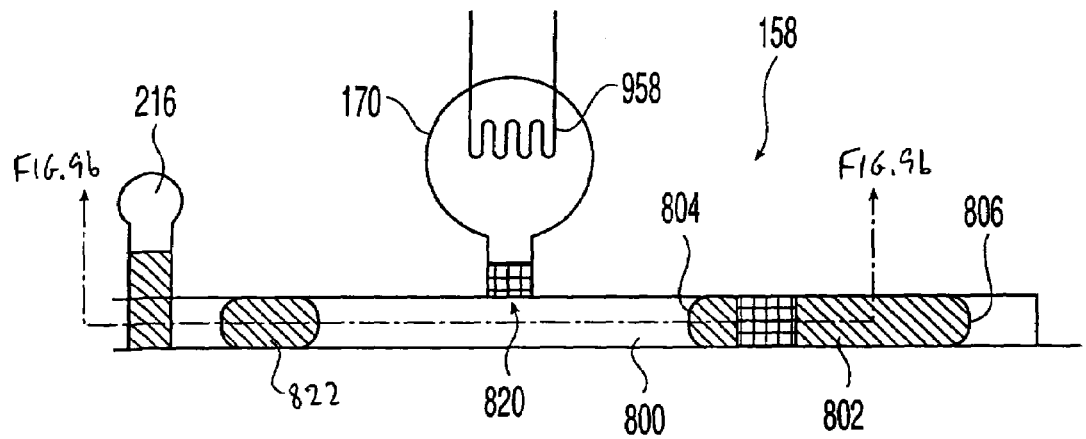
FIG. 9a shows a top view of a microdroplet preparation zone of the microfluidic device of FIG. 4 after preparation of a microdroplet.
Figure 9B:
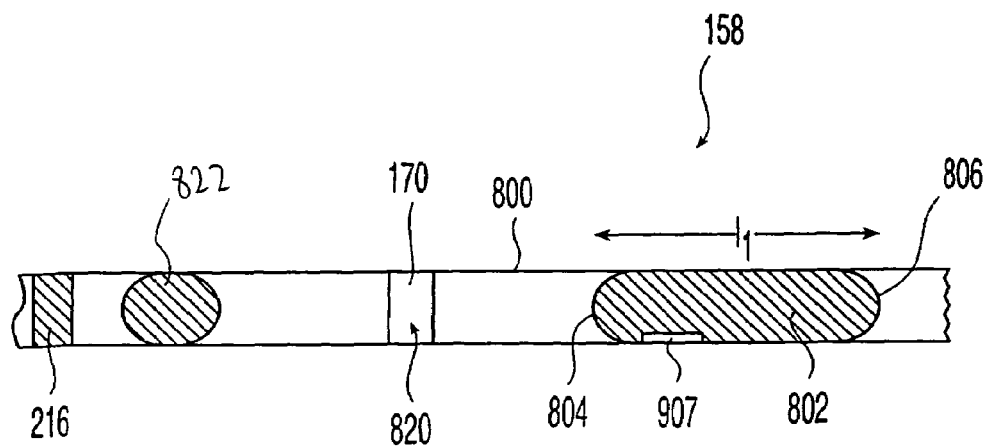

Referring to FIGS. 81a-8b, gas actuator 170 is actuated, such as by DAQ 126, to thereby generate a gas pressure sufficient to separate microdroplet 802 from the second portion 822 of microfluidic sample 808. The gas pressure is preferably provided by the actuation of a heat source 958, which heats a volume of gas associated with gas actuator 170. As the pressure increases, the gas expands, thereby separating a microdroplet 802 from the rest of sample 808. Microdroplet 802 may comprise only a portion, such as less than about 75%, or less than about 50%, of microfluidic sample 808 received by microdroplet preparation zone 800. The dimensions of microdroplet 802 are determined by the volume of the channel between fluid barrier 979 and opening 820. For example, for a channel having a uniform cross-sectional area, a length $l_1$ of microdroplet 802 corresponds to a distance $d_4$ between positioning element 979 and opening 820. Thus, a microfluidic device can be configured to prepare microdroplets of any volume by varying the length between the fluid barrier and corresponding actuator opening.

Continued actuation of gas actuator 170 overcomes the inhibitory effect of positioning element 979, thereby driving microdroplet 802 to a location downstream of microdroplet preparation zone 800 while the second portion 822 of the microfluidics sample moves upstream from microdroplet 802 to cell lysis module 160.

3. Cell Lysis Module

Referring back to FIG. 3, a lysing module 160 receives the microdroplet 802 prepared by microdroplet preparation zone 800. In general, lysing module 160 releases material from inside the particles, such as by releasing intracellular material from cells.

As shown in FIGS. 4, 12a and 12b, lysing module 160 includes a lysing zone 950, a lysing mechanism within the lysing zone (such as electrodes 954), and a vented positioning element 200 positioned upstream from the lysing zone. The lysing mechanism preferably includes a set of electrodes or other structures for generating electric fields within the lysing zone. The vented positioning element preferably includes a vent 202, a valve 204, and a second positioning element 206 for inhibiting fluid from flowing into the vent.

As explained above, actuator 170 of the microdroplet preparation module 158 drives a microdroplet into cell lysis module 160. As the microdroplet moves into module 160, vented positioning element 200 positions microdroplet 802 in a lysing position with respect to electrodes 954. More specifically, as the microdroplet arrives in lysing module 160 it passes the opening of positioning element 200, because second positioning element 206 inhibits the microdroplet from flowing into vent 202. When the rear end of the microdroplet passes the opening of barrier 200, the propulsion gas from actuator 170 dissipates through vent 202, thereby substantially equalizing gas pressure upstream of microdroplet 802 with a pressure downstream of microdroplet 802. Thus, the microdroplet stops movement at a lysing position just downstream from barrier 200. Preferably, in the lysing position, substantially all of microdroplet 802 is disposed between an upstream edge 212 and a downstream edge 214 of electrodes 954.

After microdroplet 802 is placed in the cell lysing position, a pulse circuit of DAQ 126 supplies a pulsed voltage signal across electrodes 954. In response, electrodes 954 generate a pulsed electric field in the vicinity of the electrodes. Because the microdroplet is position in this vicinity, cells within the microdroplet are subjected to the pulsed field.

Preferably, substantially all of the cells, such as greater than about 75%, of the microdroplet are subjected to an electric field sufficient to release intracellular material therefrom. The lysing module thus prepares a lysed microdroplet comprising a predetermined amount of sample.

Figure 14:
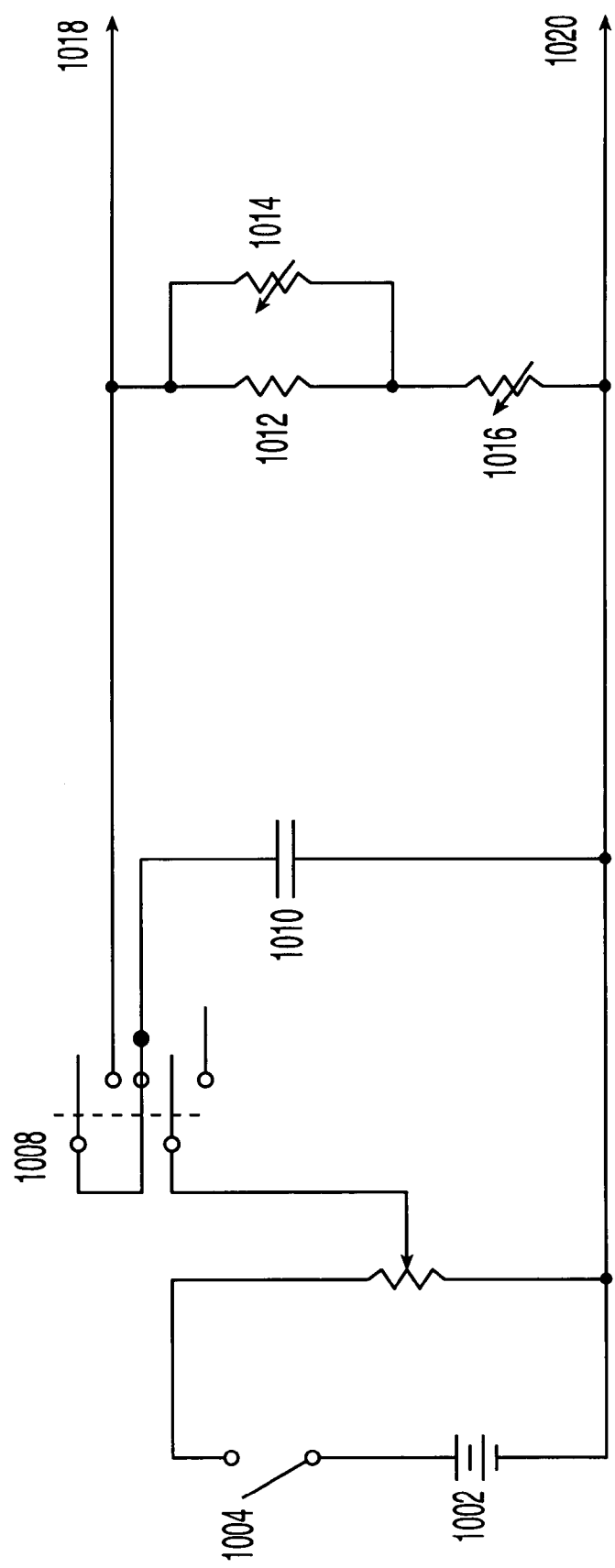
FIG. 14 shows a pulsing circuit associated with the lysing module of FIG. 4.

A preferred pulse circuit is shown in FIG. 14. In general, this circuit generates a sequence of voltage pulses that yields a corresponding sequence of electrical field pulses in the vicinity of electrodes 954 having an amplitude and duration sufficient to release a desired amount of intracellular material from cells within the microdroplet.

Intracellular material present in lysed microdroplet is accessible to further process steps. For example, DNA and/or RNA released from cells is accessible for amplification by a polymerase chain reaction. As used herein, the term lysing does not require that the cells be completely ruptured. Rather, lysing refers to the release of intracellular material. For example, rather than rupturing the cells, the electric field may increase the porosity of cell membranes by an amount that allows release of intracellular material without permanent rupture of the membranes.

Other lysing mechanisms may also be employed to release intracellular material from cells. For example, material may be released by subjecting cells to other forces including for example osmotic shock or pressure. Chemicals, selected from the group of surfactants, solvents, and antibiotics may be contacted with the cells. Mechanical shear methods may also be used to release intracellular materials.

The lysed microdroplet may be moved downstream to mixing module 160 for further processing. To move lysed microdroplet downstream, valve 216, which is disposed upstream of lysing zone 950, is closed. Valve 204 is also closed to prevent gas from exiting lysing zone 950 via vent. Actuator 170 is then actuated, as described above, to provide a gas pressure sufficient to move lysed microdroplet downstream of lysing zone 950.

In an alternative embodiment, a lysing module 300, as shown in FIGS. 13a, 13b, includes a lysing zone 302 which is configured to prepare a lysed microdroplet 304 of predetermined volume from a microfluidic sample 306, which may have an indeterminate volume. Lysing zone 302 preferably includes a lysing mechanism such as electrodes 308. Electrical leads 310 provide a connection to a pulse circuit of DAQ 126, via contacts 112, between microfluidic cartridge 110 and chip carrier 120, and contacts 125 (as shown in FIGS. 1 and 3). A positioning element 312 is disposed downstream of lysing zone 302. An actuator 314 is disposed upstream from lysing zone. Actuator 314 preferably includes a second positioning element 316 to prevent fluid from the microfluidic sample from entering therein.

Lysing zone 302 operates as follows. The microfluidic sample 306 enters lysing zone 302 and moves downstream until a downstream interface 316 of the microfluidic sample 306 encounters positioning element 312. The positioning element 312 preferably increases a surface tension of the downstream interface of the microfluidic sample 306, thereby inhibiting further downstream movement and positioning a portion of the microfluidic sample in a lysing position with respect to electrodes 308. The lysing position is defined as the location of the portion of the microfluidic sample disposed downstream of actuator 314 and upstream of positioning element 312. Preferably, actuator 314 and positioning element 312 are disposed adjacent electrodes 308 such that substantially all of the material present in the lysing position is subjected to the electric field upon actuating electrodes 308.

Actuation of electrodes 308 in the embodiment described above, provides an electrical field sufficient to release intracellular material from cells present in the portion of the microfluidic sample in the lysing position. Once a sufficient amount of intracellular material has been released, actuator 314 is actuated to prepare lysed microdroplet 304 from the microfluidic sample 306. Actuator 314 preferably provides a gas pressure sufficient to move the lysed microdroplet 304 to a downstream portion of a microfluidic device such as mixing module 166.

4. Mixing Module And Reagent Input Module

Referring back to FIG. 4, a lysed sample prepared by lysing module 160 is received by mixing module 166. Mixing module 166 includes a mixing zone 958. In this zone, the lysed cell sample is contacted, such as by mixing, with an amount of reagent received from the reagent source module 152. Reagent source module 152 includes a reagent microdroplet preparation zone (RMPZ) 434, which preferably operates to prepare a microdroplet having a predetermined volume of reagent.

a. Reagent Input Module

Reagent input module 152 is essentially the same as microdroplet formation module 158, however, it is specifically designed for formation of a microdroplet of reagent having a predetermined volume which will yield a desired ratio of reagent to sample when mixed with the microdroplet from cell lysing module 160. Module 152 includes an input port 420, a valve 422, and an actuator 172, each of which joins a reagent source channel 428. An overflow channel 424, which also joins reagents source channel 428, may also be provided. Actuator 172 may include a second positioning element 432 to prevent liquid from entering therein.

Reagent materials, which preferably comprise at least one liquid, are introduced via input port 420, such as with a pipette or syringe. Examples of suitable reagent materials include substances to facilitate further processing of the lysed cell sample, such as enzymes and other materials for amplifying DNA therein by polymerase chain reaction (PCR). The reagent material moves downstream within reagent source channel 428 until a downstream portion of the reagent material contacts a positioning element 426. Any additional reagent material that continues to be received within reagent source module preferably enters overflow channel 424. When the introduction of reagent is complete, valve 422 is closed to prevent reagent from exiting reagent source channel via reagent source port 420.

b. Mixing Module

Mixing zone 958 of the mixing module includes adjoined first and second channels 410, 412. Materials moving downstream toward mixing zone 958 contact one another and preferably mix therein. Because of the micro-scale dimensions of mixing zone 958, the sample and reagent materials preferably mix by diffusion even in the absence of other sources of mass transport, such as mechanical agitation. It should be understood however, that agitation forces, such as acoustic waves may be applied to enhance mixing within mixing zone 958.

c. Operation of Mixing Module and Reagent Input Module

Reagent source module 152 and mixing module 166 preferably operate as follows. When a lysed sample from lysing zone 950 is ready to be mixed with reagent material, actuator 172 is actuated to prepare a microdroplet of reagent. The microdroplet of reagent is prepared from the portion of reagent material downstream of an opening 430 of actuator 172 and upstream of positioning element 427. Thus, assuming that the dimensions of the reagent source channel 428 are constant, the volume of the microdroplet of reagent is determined by the distance between the positioning element 426 and the actuator opening 430.

The microdroplet of reagent moves downstream toward channel 412 of reagent mixing zone. Meanwhile, a sample of lysed material, such as a lysed microdroplet, is moved downstream from lysing zone 950 toward channel 410 of mixing zone 958. Actuator 170 may provide the motive force to move the lysed microdroplet downstream. Alternatively, as discussed above, another actuator may be disposed upstream of lysing zone 950 but downstream of actuator 170 to provide the necessary motive force.

The sample and reagent material enter a downstream channel 438 of mixing zone 958, where the materials contact and mix. Because both the lysed sample and reagent material are mixed in the form of microdroplets, mixing zone 958 prepares an amount of mixed material having a predetermined ratio of sample to reagent. The volumes of microdroplets prepared within microfluidic device 110 are preferably independent of physical properties, such as viscosity, electrical conductivity, and osmotic strength, of the microdroplets. Thus, mixing zone 958 prepares an amount of mixed material having a sample to reagent material that is also independent of the physical and chemical properties of the mixed materials. A vent 440, which is downstream of the various zones of the microfluidic device 110 ensures that downstream pressure buildup does not inhibit downstream movement of samples within microfluidic device 110.

5. DNA Manipulation Module

The mixed lysed cell sample and reagent are received within a DNA manipulation zone 971 of DNA manipulation module 162. Module 162 can perform, for example, restriction, digestion, ligation, hybridization and amplification of DNA material. In one embodiment, DNA manipulation zone 971 is configured to perform PCR amplification of nucleic acids present within the lysed cell sample. Vent 440 prevents pressure from increasing within zone 971 as the lysed cell sample and reagent are being introduced thereto. Valves 972 and 973 of DNA manipulation module 162 may be closed to prevent substances therein zone from exiting, such as by evaporation, during PCR amplification. The DNA manipulation zone is configured with heat sources under control of computer 127 to allow thermal cycling of DNA manipulation zone during amplification, as understood by one of skill in the art.

System 901 includes also includes a detector 981 to detect the presence of amplified polynucleotides produced by PCR. Detector 981 is preferably an optical detector in optical communication, such as by a fiber optic 981, with zone 971. A light source, such as a laser diode, introduces light to DNA Manipulation zone 971 to generate fluorescence indicative of the amount of amplified polynucleotides present therein. The fluorescence arises from fluorescent tags, included in the reagent and associated with the polynucleotides upon amplification.

C. Preferred Positioning Elements

Preferred positioning elements are discussed below.

1. Non-Wetting Positioning Elements

A positioning element 979 may be formed by a non-wetting material disposed to contact a microfluidic sample. The physico-chemical properties of the non-wetting material are chosen upon considering the type of liquid forming the microfluidic sample. For example, where the microfluidic sample is an aqueous sample, the positioning element preferably comprises a hydrophobic material. An exemplary hydrophobic material includes a non-polar organic compound, such as an aliphatic silane, which can be formed by modifying an internal surface of microfluidic device 901. For microfluidic samples formed of organic solvents, the non-wetting material may comprise a hydrophilic material.

When microfluidic sample 808 encounters positioning element 979, the liquid of the microfluidic sample experiences an increased surface tension at downstream interface 810, which increased surface tension inhibits continued downstream motion of microfluidic sample 808. Increasing the gas pressure difference between upstream and downstream portions of the microfluidic sample overcomes the resistance and moves the microfluidic sample downstream.

2. Capillary Assisted Positioning Elements

Figure 10A:
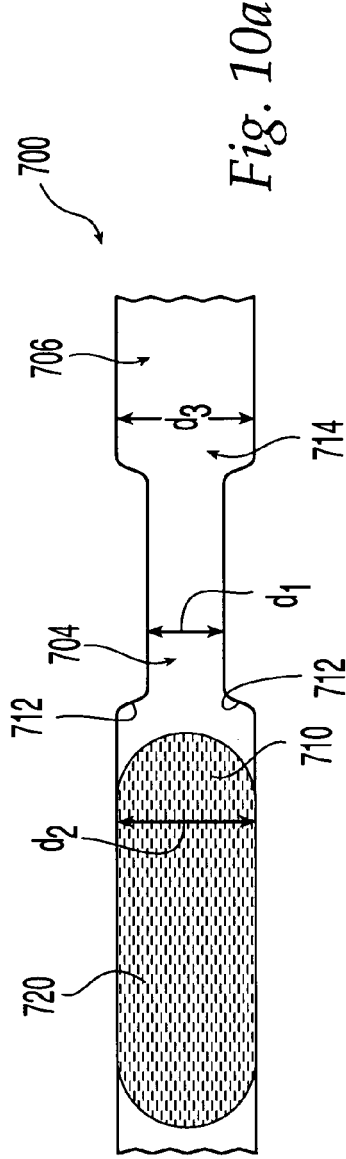
FIGS. 10a-10c show cross sectional side views of a capillary assisted fluid barrier of the present invention.
Figure 10B:
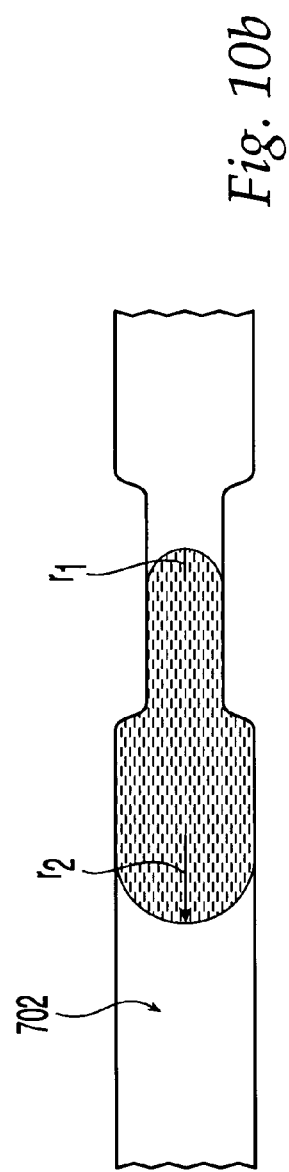
Figure 10C:
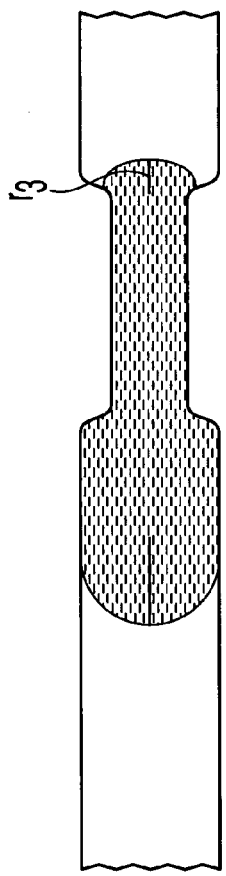

Referring to FIGS. 10a-10c, another type of positioning element may be formed by modifying the dimensions of the microfluidic channel to form a capillary assisted positioning element (CAFB) 700. A CAFB comprises an upstream feed zone 702, a loading zone 704, and a stop zone 706. A microfluidic sample 720 encountering the CAFB moves downstream until a downstream interface 710 of the microfluidic sample contacts upstream surfaces 212 of the loading zone 704. At this point, capillary action causes the microfluidic sample to move downstream until the downstream sample interface 710 encounters the opening 714 between the loading zone 704 and the stop zone 706. Surface tension resists the tendency of the microfluidic sample to continue downstream past opening 714. Thus, the microfluidic sample 720 is positioned at a predetermined location along the channel axis with respect to positioning element 700.

The volume of the microfluidic sample encountering the CAFB preferably has a larger volume than a volume of the loading zone 704 to ensure that the microfluidic sample will advance fully to opening. For fluids that have similar surface tensions and interface properties as water, the depth $d_1$ of the loading zone 704 is preferably about 50% or less of the respective depths $d_2$, $d_3$ of the feed and stop zones.

The tendency of a microfluidic sample to move in a given direction is governed by the ratio between the mean radius of curvature (MRC) of the front of the microfluidic sample and the MRC of the back of the microfluidic sample. These curvatures depend upon the contact angle of the fluid of the sample and the dimensions of the zone in which the microdroplet is moving. A MRC $r_1$ of a microdroplet interface in the loading zone is preferably smaller than a MRC $r_2$ of a droplet interface within the feed zone or a MRC $r_3$ of a droplet interface within the stop zone. The MRC $r_2$ is preferably larger than the MRC $r_3$. Thus, the radius of curvature of the downstream microdroplet interface increases upon encountering the stop zone thereby inhibiting further downstream movement. Preferably, the contact angle of the fluid with the wall is substantially constant throughout the capillary assisted loading zone.

3. Vented Positioning Elements

Figure 11A:
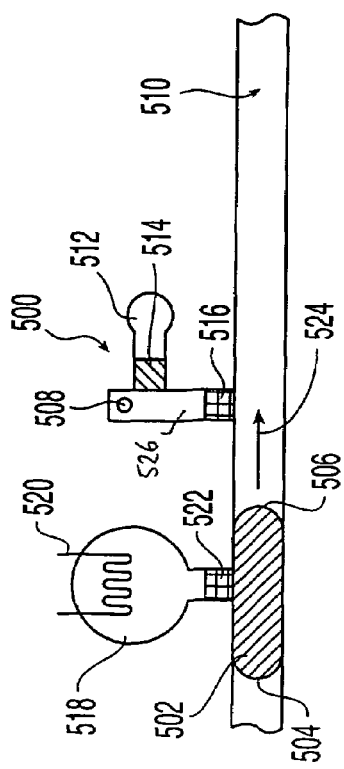
FIGS. 11a-11c show top views of a fluid barrier comprising a vent.
Figure 11B:
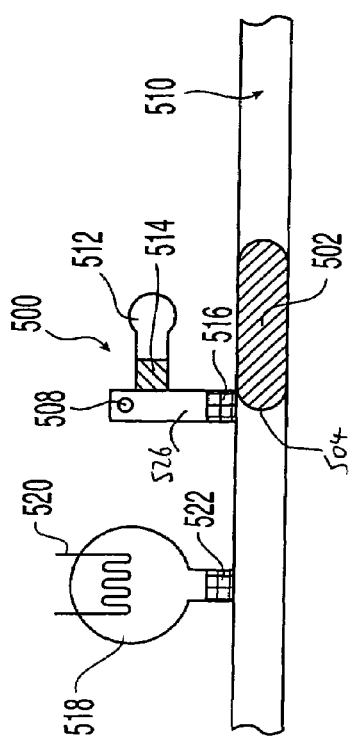
Figure 11C:
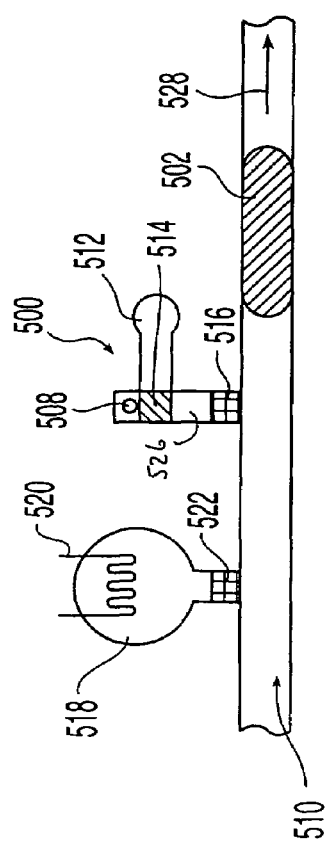

Referring to FIGS. 11a-11c, a positioning element 500 operates to position a microfluidic sample 502 by reducing the gas pressure acting upon an upstream portion 504 of the microfluidic sample relative to the gas pressure acting upon a downstream portion 506 of the microfluidic sample. Positioning element 500 includes a vent 508 disposed in gaseous communication with a zone 510 along which microfluidic sample 502 moves. Vent 508 preferably communicates with zone 510 via a passage 526. The zone may be for example, a channel or conduit. Positioning element 500 may also include a second positioning element 516, such as a non-wetting material, to substantially prevent fluid from the microfluidic sample from contacting the vent.

An open state of a valve 512 allows passage of gas between zone 510 and vent 508. A closed state of valve 512 prevents such passage of gas. Valve 512 is preferably thermally actuated and includes a mass 514 of thermally responsive substance (TRS).

An actuator 518 is disposed upstream of positioning element 500. Actuator 518 is preferably a gas actuator and may include a heat source 520 to heat a gas associated with actuator 518. Actuator 518 may include a positioning element 522, such as non-wetting material, to substantially prevent fluid from the microfluidic sample from entering therein.

Positioning element 500 preferably operates as follows. Referring to FIG. 11a, microfluidic sample 502 moves downstream in the direction of arrow 524. Microfluidic sample is preferably moved by a gas pressure provided from an upstream actuator, which is not shown in FIGS. 11a-11c. The gas pressure acts upon upstream portion 504.

Referring to FIG. 11b, when upstream portion 504 passes the opening of vent 508, the upstream gas dissipates through vent 508, thereby reducing the upstream pressure. The pressure reduction, which preferably equalizes the downstream and upstream pressures, reduces or eliminates the motive force tending to urge the microfluidic sample downstream.

Referring to FIG. 11c, valve 512 is closed to prevent passage of gas between zone 510 and vent 508. Preferably, TRS 514 moves into passage 526. Upon closing valve 512, the actuation of actuator 518 provides a motive force to move microfluidic sample 502 downstream in the direction of arrow 528 for further processing.

4. Active Fluid Positioning Elements

Figure 15A:
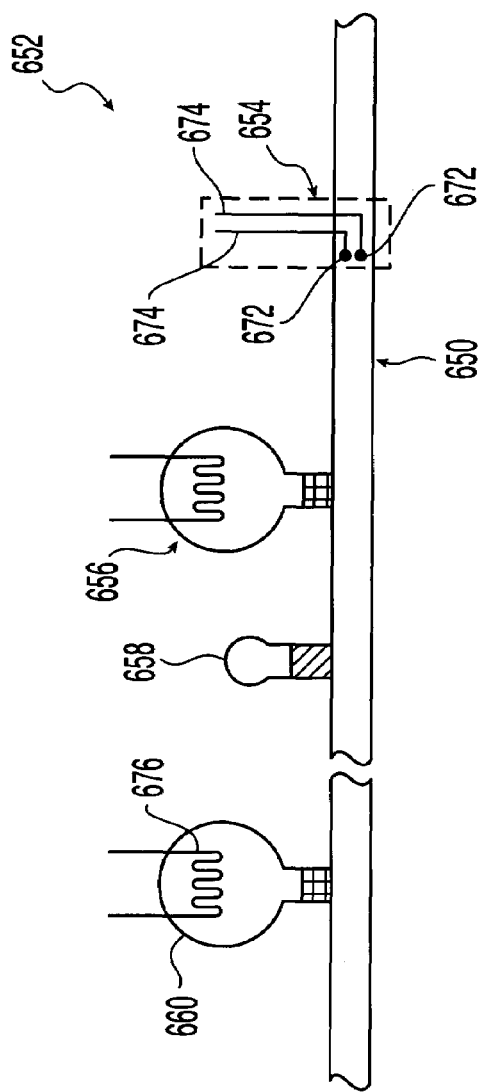
FIGS. 15a-15c show a second microdroplet preparation module of the invention.
Figure 15B:
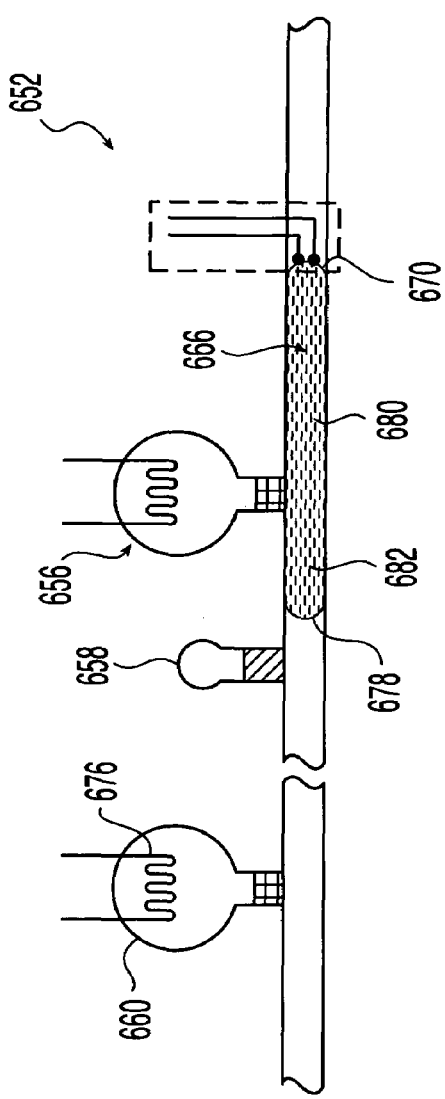
Figure 15C:
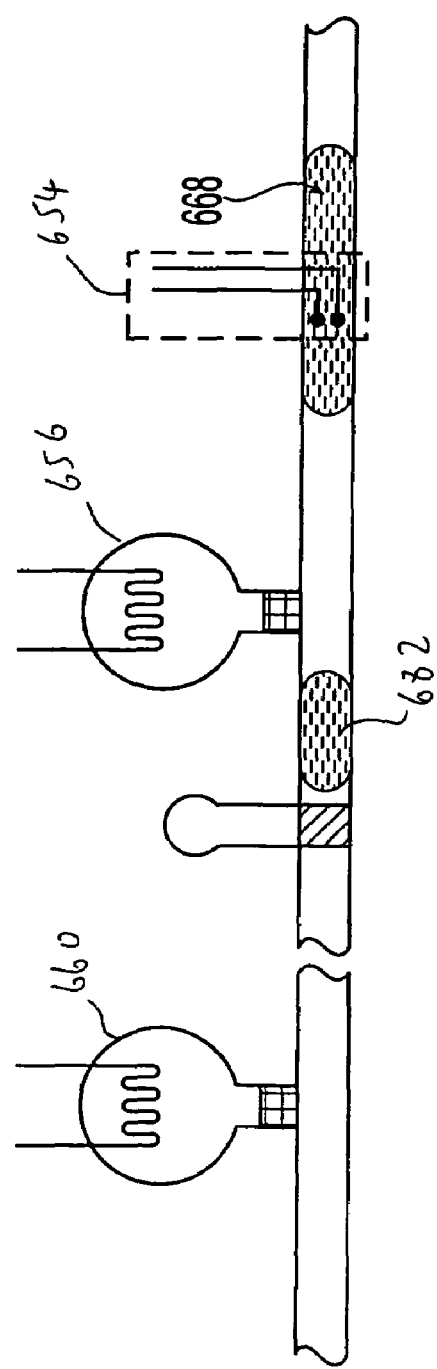

Referring to FIGS. 15a-15c, a microdroplet preparation module 652 has a microdroplet preparation zone 650, an active fluid positioning element 654, an actuator 656, and a valve 658. A second actuator 660 is operatively associated with the active positioning element 654 to introduce a microfluidic sample 666 to the microdroplet preparation zone 650. Second actuator 660 is preferably located upstream from valve 658. Microdroplet preparation module 652 prepares a microdroplet 668, which has a predetermined volume from the microfluidic sample 666 received therein.

In operation, microfluidic preparation module 652 receives the microfluidic sample 666, which moves downstream because of a motive force provided by the second actuator 660. The motive force is preferably an upstream gas pressure, which is greater than a downstream gas pressure acting upon the microfluidic sample 666. The microfluidic sample moves downstream until a downstream portion 670 thereof encounters active positioning element 654, which preferably comprises a sensor 672 having electrical leads 674. The leads 674 are in electrical communication with I/O pins of the microfluidic device to allow signals from sensor 672 to be received by a DAQ.

Sensing element 672 is preferably a pair of electrical contacts. To sense the presense of the liquid, DAQ 126 applies a small voltage across leads 674 and measures the resultant current. As the liquid of the microfluidic sample contacts the first and second contacts, the current passing therebetween changes, thereby indicating to DAQ 126 that the liquid has arrived at sensor 672.

Upon recognition that the liquid has arrived at sensor 672, the DAQ instructs second actuator 660 to decrease a downstream motive force acting upon the microfluidic sample 666. For example, DAQ may reduce a current flowing through a heat source 676 associated with second actuator 660 thereby reducing a temperature of a gas therein. The temperature reduction reduces the gas pressure acting upon a upstream portion 678 of microfluidic sample thereby inhibiting the downstream motion of the microfluidic sample 666. The microfluidic sample is positioned such that a first portion 680 is located downstream of actuator 656 and a second portion 682 is located upstream of actuator 656.

To prepare microdroplet 668, DAQ 126 actuates actuator 656 to provide a motive force which prepares the microdroplet 668 from the first portion 680 of microfluidic sample 666. Microdroplet 668 moves downstream while the second portion 682 of the microfluidic sample 666 moves upstream from actuator 656. During microdroplet preparation, valve 658 may be closed to substantially isolate the actuator 656 from second actuator 660 and other upstream portions of the microfluidic device.

The active positioning element preferably operates as a closed loop element that provides feedback from sensor 672 to the DAQ. The feedback is indicated when a microfluidic sample has reached a predetermined position within the microfluidic device. Upon receiving the feedback, the DAQ changes the state of the actuator providing the motive force to move the microdroplet.

D. Multiple Actuators

The various actuators of microfluidic device 110 provide an example of how multiple actuators may cooperate to move material between different locations of microfluidic device 110. For example, actuator 168 moves material, such as an enriched sample, between enrichment zone 931 and microdroplet preparation module 158. Actuator 170 prepares a microdroplet from the enriched sample and, in so doing, moves the microdroplet to the lysing zone 950. Actuator 170 is used to move material from the lysing zone 950 to mixing module 166. It should be noted, however, that another actuator may be disposed intermediate between lysing zone 950 and microdroplet preparation zone to move the lysed sample downstream to the mixing module 166.

Actuators of device 110 may also cooperate in moving two amounts of material simultaneously. For example, as described above, actuator 172 and actuator 170 cooperate to mix reagent and lysed microdroplets. Such cooperative actuators can be controlled independently of one another to ensure proper mixing. For example, if one material is known to be more viscous, the motive force moving that material can be increased independently of the motive force moving the other material.

The multiple actuators and modules of microfluidic device 110 are preferably operatively connectable and isolatable by the valves of microfluidic device. For example, a closed state of either of valves 915, 216 operatively isolates microdroplet preparation module 170 from enrichment module 156. Thus, one or more actuators can be used to move materials between predetermined locations within microfluidic device 110, without perturbing or contacting material present in an operatively isolated module. The ability to operatively connect and isolate desired modules is advantageous in microfluidic devices having many process functions. Further, these valves also control the direction of the propulsive force of the actuators by preventing the expanding gas from traveling in certain directions, while permitting it to expand in the desired direction. This also extends the range over which an actuator can propel a microdroplet, by preventing the gas from dissipating in certain areas upstream from the microdroplet.

While the above invention has been described with reference to certain preferred embodiments, it should be kept in mind that the scope of the present invention is not limited to these. Thus, one skilled in the art may find variations of these preferred embodiments which, nevertheless, fall within the spirit of the present invention, whose scope is defined by the claims set forth below.

What is claimed is:

1. A microfluidic device, comprising:
    an enrichment module configured to receive a microdroplet of particle-containing fluid, the enrichment module comprising a flow-through member and an enrichment chamber, wherein the flow-through member is configured to allow fluid of the particle-containing fluid to pass through the flow-through member thereby accumulating an enriched particle sample, comprising particles of the particle-containing fluid, in the enrichment chamber;
    a downstream channel leading downstream from the enrichment chamber to at least one downstream processing module;
    an actuator configured to move the enriched particle sample downstream from the enrichment module along the downstream channel; and
    a first valve disposed between the actuator and the flow-through member.

2. The micro fluidic device of claim 1, wherein the flow-through member is configured to sieve particles from the particle-containing fluid.

3. The microfluidic device of claim 1, further comprising a second valve disposed between the flow-through member and the downstream channel.

4. The microfluidic device of claim 3, wherein the actuator is a gas actuator, and the device is configured to move the enriched particle sample from the enrichment chamber to the downstream channel by opening the first and second valves and actuating the gas actuator to thereby increase a gas pressure within the enrichment chamber relative to a gas pressure within the downstream channel.

5. The microfluidic device of claim 3, wherein the device comprises a lower substrate and an upper substrate, and wherein the enrichment module, downstream channel, first valve, second valve, and actuator are integral with the upper substrate.

6. The microfluidic device of claim 3, wherein the actuator is a gas actuator and the device is configured to move the enriched particle sample from the enrichment chamber to the downstream channel by opening the first and second valves and actuating the gas actuator to thereby decrease a gas pressure within the downstream channel relative to a gas pressure in the enrichment chamber.

7. The micro fluidic device of claim 1, wherein the at least one downstream processing module includes a mixing zone configured to combine a predetermined portion of the enriched particle sample with a predetermined amount of a reagent.

8. The microfluidic device of claim 7, wherein the mixing zone is configured to combine only a portion of the enriched particle sample received by the downstream channel with the predetermined amount of reagent.

9. The microfluidic device of claim 1, wherein the at least one downstream processing module includes a lysing module comprising a source of electrical energy to lyse cells in the enriched particle sample.

10. The microfluidic device of claim 9, wherein said lysing module includes a positioning element to position the enriched particle sample in a lysing position with respect to the lysing zone.

11. The microfluidic device of claim 1, wherein the at least one downstream processing module includes a DNA manipulation zone configured to subject the enriched particle sample and a reagent to polymerase chain reaction to provide amplified polynucleotides.

12. The microfluidic device of claim 1, further comprising a sample input module connected to the flow-through member via a sample introduction channel.

13. The device of claim 5, wherein the flow-through member has first and second surfaces, wherein the first surface is adjacent the enrichment chamber, and the second surface is spaced apart from the enrichment chamber and is adjacent a self-contained space, wherein the self-contained space contains an absorbent material and is disposed in the upper substrate on a surface of the upper substrate opposite to the lower substrate.

14. The device of claim 5, wherein:
the lower substrate has a glass base and an oxide layer, wherein the oxide layer contains a plurality of resistive heaters;
and wherein the upper substrate has a bottom surface, bonded to the oxide layer on the lower substrate.

15. The microfluidic device of claim 1, wherein the actuator is a thermally actuated gas actuator.

16. The microfluidic device of claim 14, wherein the actuator is integral with the upper substrate.

17. The microfluidic device of claim 14, wherein the actuator is a thermally actuated gas actuator and comprises a resistive heater located beneath a chamber in the upper substrate.

18. The microfluidic device of claim 17, wherein the resistive heater is in thermal contact with the chamber, and wherein the chamber contains a volume of gas.

19. The microfluidic device of claim 3, wherein the first and second valves are thermally actuated.

20. The microfluidic device of claim 3, wherein the first and second valves are reversible between an open and a closed state.

21. The microfluidic device of claim 3, wherein the first and second valves comprise a thermally responsive substance.

22. The device of claim 1, wherein the flow-through member comprises a material having pathways smaller than the diameter of particles in the particle containing fluid.

23. The microfluidic device of claim 22, wherein the flow-through member has pores of less than about 2 microns in diameter.

24. The microfluidic device of claim 22, wherein the flow-through member is made from a material selected from the group consisting of: paper, textiles, polymers having a network of pathways, and glassy materials.

25. The microfluidic device of claim 1, wherein the enriched particle sample has a substantially higher ratio of particles per volume of fluid than a corresponding ratio of the particle containing fluid.

26. The microfluidic device of claim 25, wherein the ratio is about 250.

27. A microfluidic device, comprising:
an enrichment module configured to separate an enriched particle sample from a microdroplet of particle-containing fluid, wherein the enrichment module comprises a flow-through member and an enrichment chamber;
a processing module disposed downstream of the enrichment module;
an actuator configured to move the enriched particle sample downstream from the enrichment module with essentially no dilution of the enriched particle sample; and
a first valve disposed between the actuator and the flow-through member.

28. The microfluidic device of claim 27, wherein the flow-through member is configured to substantially prevent passage of particles of the particle-containing fluid while allowing liquid of the particle-containing fluid to exit the enrichment module.

29. The microfluidic device of claim 28, wherein the flow-through member is configured to sieve particles from the particle-containing fluid.

30. The microfluidic device of claim 27 further comprising a second valve disposed between the flow-through member and the processing module.

31. The microfluidic device of claim 30 wherein the device is configured to move the enriched particle sample downstream from the enrichment module by opening the first and second valves and actuating the actuator.

32. The microfluidic device of claim 30, wherein the first and second valves are thermally actuated.

33. The microfluidic device of claim 30, wherein the first and second valves are reversible between an open and a closed state.

34. The microfluidic device of claim 30, wherein the first and second valves comprise a thermally responsive substance.

35. The microfluidic device of claim 27, wherein the device further comprises a substrate, and the enrichment module, first valve, and actuator are integral with the substrate.

36. The microfluidic device of claim 27, wherein the actuator is a gas actuator and is configured to drive a volume of gas against an upstream portion of the enriched particle sample.

37. The microfluidic device of claim 27, wherein the processing module includes a lysing module, and wherein said lysing module includes a positioning element to position the enriched particle sample in a lysing position with respect to the lysing zone.

38. The microfluidic device of claim 27, wherein the lysing module comprises a source of electrical energy to lyse cells in the sample.

39. The microfluidic device of claim 27, wherein the actuator is a thermally actuated gas actuator.

40. The microfluidic device of claim 27, wherein the processing module comprises a DNA manipulation module configured to subject the enriched particle sample and a reagent to a polymerase chain reaction thereby providing amplified polynucleotides.

41. The microfluidic device of claim 40, wherein the device comprises a substrate and the enrichment module and DNA manipulation module are integral with the substrate.

42. The microfluidic device of claim 27, wherein the flow-through member comprises a material having pathways smaller than the diameter of particles in the microdroplet of particle containing fluid.

* * * * *